US012746140B2

(12) United States Patent
Petursson et al.

(10) Patent No.: US 12,746,140 B2
(45) Date of Patent: Sep. 29, 2026

(54) CONNECTOR FOR AN ORTHOPEDIC DEVICE

(71) Applicant: OSSUR ICELAND EHF, Reykjavik (IS)

(72) Inventors: Valgeir Petursson, Reykjavik (IS); Halldor Albertsson, Reykjavik (IS)

(73) Assignee: OSSUR ICELAND EHF, Reykjavik (IS)

( * ) Notice: Subject to any disclaimer, the term of this patent is extended or adjusted under 35 U.S.C. 154(b) by 180 days.

(21) Appl. No.: 18/329,728

(22) Filed: Jun. 6, 2023

(65) Prior Publication Data

US 2023/0310195 A1 Oct. 5, 2023

Related U.S. Application Data

(63) Continuation of application No. 16/154,199, filed on Oct. 8, 2018, now Pat. No. 11,712,359.

(60) Provisional application No. 62/649,104, filed on Mar. 28, 2018, provisional application No. 62/568,935, filed on Oct. 6, 2017.

(51) Int. Cl.
*A61F 5/01* (2006.01)
*A61F 5/05* (2006.01)

(52) U.S. Cl.
CPC .... *A61F 5/0123* (2013.01); *A61F 2005/0148* (2013.01); *A61F 2005/0158* (2013.01); *A61F 2005/0172* (2013.01); *A61F 2005/0181* (2013.01); *A61F 5/05* (2013.01)

(58) Field of Classification Search
CPC .... A61F 5/0104; A61F 5/0106; A61F 5/0123; A61F 5/0125; A61F 2005/0146; A61F 2005/0148; A61F 2005/0153; A61F 2005/0158; A61F 2005/0172; A61F 2005/0174; A61F 2005/0176; A61F 2005/0181; A61F 5/05
See application file for complete search history.

(56) References Cited

U.S. PATENT DOCUMENTS

| | | | |
|---|---|---|---|
| 667,768 | A | 2/1901 | De Puy |
| 777,585 | A | 12/1904 | Beatty |
| 937,478 | A | 10/1909 | Sims |
| 1,153,334 | A | 9/1915 | Oswald |
| 1,227,700 | A | 5/1917 | Hamilton |
| 1,328,541 | A | 1/1920 | Palmer |

(Continued)

FOREIGN PATENT DOCUMENTS

| | | | |
|---|---|---|---|
| CN | 101128169 | A | 2/2008 |
| DE | 0846895 | C | 8/1952 |

(Continued)

OTHER PUBLICATIONS

"Information on Flexible Polyurethane Foam", In Touch, vol. 4, No. 3, Jul. 1994, 5 pages.

(Continued)

*Primary Examiner* — Alireza Nia
*Assistant Examiner* — Gina McCarthy
(74) *Attorney, Agent, or Firm* — Workman Nydegger

(57) ABSTRACT

A connector for a strap includes a buckle assembly having a base part, and a strap mount flexibly depending from the buckle assembly. The strap mount is integrally connected to the base part such that the base part is rigid when the strap mount bends relative thereto.

19 Claims, 22 Drawing Sheets

(56) References Cited

U.S. PATENT DOCUMENTS

| | | | |
|---|---|---|---|
| 1,510,408 | A | 9/1924 | Lychou |
| 1,593,631 | A | 7/1926 | Harsh |
| 1,622,211 | A | 3/1927 | Sheehan |
| 1,825,898 | A | 10/1931 | Coulter |
| 2,032,923 | A | 3/1936 | Eldridge |
| 2,179,903 | A | 11/1939 | Spears |
| 2,467,907 | A | 4/1949 | Peckham |
| 2,573,866 | A | 11/1951 | Murphy |
| 2,717,841 | A | 9/1955 | Biefeld et al. |
| 2,935,065 | A | 5/1960 | Homier et al. |
| 3,031,730 | A | 5/1962 | Morin |
| 3,046,981 | A | 7/1962 | Biggs et al. |
| 3,089,486 | A | 5/1963 | Pike |
| 3,266,113 | A | 8/1966 | Flanagan, Jr. |
| 3,463,147 | A | 8/1969 | Stubbs |
| 3,514,313 | A | 5/1970 | Martel et al. |
| 3,520,765 | A | 7/1970 | Bateman |
| 3,528,412 | A | 9/1970 | McDavid |
| 3,561,436 | A | 2/1971 | Gaylord, Jr. |
| 3,581,741 | A | 6/1971 | Rosman et al. |
| 3,594,863 | A | 7/1971 | Erb |
| 3,594,865 | A | 7/1971 | Erb |
| 3,742,557 | A | 7/1973 | Francois |
| 3,752,619 | A | 8/1973 | Harvey et al. |
| 3,758,657 | A | 9/1973 | Menzin et al. |
| 3,789,842 | A | 2/1974 | Froimson |
| 3,804,084 | A | 4/1974 | Lehman |
| 3,817,244 | A | 6/1974 | Taylor |
| 3,851,357 | A | 12/1974 | Ribich et al. |
| 3,877,426 | A | 4/1975 | Nirschl |
| 3,916,077 | A | 10/1975 | Damrau |
| 3,927,881 | A | 12/1975 | Lemelson et al. |
| 3,945,046 | A | 3/1976 | Stromgren |
| 3,955,565 | A | 5/1976 | Johnson, Jr. |
| 4,130,115 | A | 12/1978 | Taylor |
| 4,193,395 | A | 3/1980 | Gruber |
| 4,204,532 | A | 5/1980 | Lind et al. |
| 4,240,414 | A | 12/1980 | Theisler |
| 4,269,179 | A | 5/1981 | Burton et al. |
| 4,269,181 | A | 5/1981 | Delannoy |
| 4,275,716 | A | 6/1981 | Scott, Jr. |
| 4,280,489 | A | 7/1981 | Johnson, Jr. |
| 4,291,072 | A | 9/1981 | Barrett et al. |
| 4,296,744 | A | 10/1981 | Palumbo |
| 4,304,560 | A | 12/1981 | Greenwood |
| 4,312,335 | A | 1/1982 | Daniell, Jr. |
| 4,336,279 | A | 6/1982 | Metzger |
| 4,372,298 | A | 2/1983 | Lerman |
| 4,381,768 | A | 5/1983 | Erichsen et al. |
| 4,381,769 | A | 5/1983 | Prahl |
| 4,386,723 | A | 6/1983 | Mule |
| 4,396,012 | A | 8/1983 | Cobiski |
| 4,470,857 | A | 9/1984 | Casalou |
| 4,472,461 | A | 9/1984 | Johnson |
| 4,506,661 | A | 3/1985 | Foster |
| 4,528,440 | A | 7/1985 | Ishihara |
| 4,554,913 | A | 11/1985 | Womack et al. |
| 4,556,053 | A | 12/1985 | Irons |
| 4,572,170 | A | 2/1986 | Cronk et al. |
| 4,617,214 | A | 10/1986 | Billarant |
| 4,632,098 | A | 12/1986 | Grundei et al. |
| 4,677,713 | A | 7/1987 | Copp |
| 4,693,921 | A | 9/1987 | Billarant et al. |
| D292,529 | S | 10/1987 | Saare |
| 4,697,583 | A | 10/1987 | Mason et al. |
| 4,724,831 | A | 2/1988 | Huntjens |
| 4,768,500 | A | 9/1988 | Mason et al. |
| 4,775,310 | A | 10/1988 | Fischer |
| D298,568 | S | 11/1988 | Womack et al. |
| 4,782,605 | A | 11/1988 | Chapnick |
| 4,791,916 | A | 12/1988 | Paez |
| 4,794,028 | A | 12/1988 | Fischer |
| 4,801,138 | A | 1/1989 | Airy et al. |
| 4,802,939 | A | 2/1989 | Billarant et al. |
| 4,805,606 | A | 2/1989 | McDavid, III |
| 4,854,308 | A | 8/1989 | Drillio |
| 4,856,501 | A | 8/1989 | Castillo et al. |
| 4,856,502 | A | 8/1989 | Ersfeld et al. |
| 4,872,243 | A | 10/1989 | Fischer |
| 4,922,929 | A | 5/1990 | DeJournett |
| 4,933,035 | A | 6/1990 | Billarant et al. |
| 4,953,543 | A | 9/1990 | Grim et al. |
| 4,961,544 | A | 10/1990 | Bidoia |
| 4,966,133 | A | 10/1990 | Kausek |
| 4,989,593 | A | 2/1991 | Campagna et al. |
| 4,991,574 | A | 2/1991 | Pocknell |
| 4,991,640 | A | 2/1991 | Verkindt et al. |
| 5,005,527 | A | 4/1991 | Hatfield |
| 5,005,627 | A | 4/1991 | Tannehill |
| 5,016,621 | A | 5/1991 | Bender |
| 5,018,514 | A | 5/1991 | Grood et al. |
| 5,020,196 | A | 6/1991 | Panach et al. |
| 5,022,109 | A | 6/1991 | Pekar |
| 5,063,916 | A | 11/1991 | France et al. |
| 5,067,772 | A | 11/1991 | Koa |
| 5,077,870 | A | 1/1992 | Melbye et al. |
| 5,085,210 | A | 2/1992 | Smith, III |
| 5,112,296 | A | 5/1992 | Beard et al. |
| 5,154,682 | A | 10/1992 | Kellerman |
| 5,157,813 | A | 10/1992 | Carroll |
| 5,181,331 | A | 1/1993 | Berger |
| 5,227,698 | A | 7/1993 | Simpson et al. |
| 5,242,379 | A | 9/1993 | Harris et al. |
| 5,267,951 | A | 12/1993 | Ishii |
| 5,277,697 | A | 1/1994 | France et al. |
| 5,277,698 | A | 1/1994 | Taylor |
| 5,288,287 | A | 2/1994 | Castillo et al. |
| 5,302,169 | A | 4/1994 | Taylor |
| 5,306,230 | A | 4/1994 | Bodine |
| 5,314,455 | A | 5/1994 | Johnson et al. |
| 5,316,547 | A | 5/1994 | Gildersleeve |
| 5,322,729 | A | 6/1994 | Heeter et al. |
| 5,334,135 | A | 8/1994 | Grim et al. |
| 5,344,135 | A | 9/1994 | Isobe et al. |
| 5,368,549 | A | 11/1994 | McVicker |
| 5,383,845 | A | 1/1995 | Nebolon |
| 5,397,296 | A | 3/1995 | Sydor et al. |
| 5,415,625 | A | 5/1995 | Cassford et al. |
| 5,431,623 | A | 7/1995 | Rice |
| 5,437,619 | A | 8/1995 | Malewicz et al. |
| 5,445,602 | A | 8/1995 | Grim et al. |
| 5,449,341 | A | 9/1995 | Harris |
| 5,458,565 | A | 10/1995 | Tillinghast et al. |
| 5,468,219 | A | 11/1995 | Crippen |
| 5,472,413 | A | 12/1995 | Detty |
| 5,474,524 | A | 12/1995 | Carey |
| 5,497,513 | A | 3/1996 | Arabeyre et al. |
| 5,500,268 | A | 3/1996 | Billarant |
| 5,512,039 | A | 4/1996 | White |
| 5,513,658 | A | 5/1996 | Goseki |
| 5,514,081 | A | 5/1996 | Mann |
| 5,527,269 | A | 6/1996 | Reithofer |
| 5,540,982 | A | 7/1996 | Scholz et al. |
| 5,542,911 | A | 8/1996 | Cassford et al. |
| 5,562,605 | A | 10/1996 | Taylor |
| 5,599,288 | A | 2/1997 | Shirley et al. |
| 5,614,045 | A | 3/1997 | Billarant |
| 5,624,389 | A | 4/1997 | Zepf |
| 5,635,201 | A | 6/1997 | Fabo |
| 5,638,588 | A | 6/1997 | Jungkind |
| 5,654,070 | A | 8/1997 | Billarant |
| 5,656,226 | A | 8/1997 | McVicker |
| 5,665,449 | A | 9/1997 | Billarant |
| 5,695,452 | A | 12/1997 | Grim et al. |
| 5,713,837 | A | 2/1998 | Grim et al. |
| D392,877 | S | 3/1998 | Eguchi |
| 5,737,854 | A | 4/1998 | Sussmann |
| 5,759,167 | A | 6/1998 | Shields et al. |
| 5,769,808 | A | 6/1998 | Matthijs et al. |
| 5,774,902 | A | 7/1998 | Gehse |
| 5,795,640 | A | 8/1998 | Billarant |
| 5,807,294 | A | 9/1998 | Cawley et al. |
| 5,823,931 | A | 10/1998 | Gilmour |
| 5,823,981 | A | 10/1998 | Grim et al. |

(56) References Cited

U.S. PATENT DOCUMENTS 5,840,398 A 11/1998 Billarant
5,857,988 A 1/1999 Shirley
5,857,989 A 1/1999 Smith, III
5,865,776 A 2/1999 Springs
5,865,777 A 2/1999 Detty
5,865,782 A 2/1999 Fareed
5,873,848 A 2/1999 Fulkerson
5,891,061 A 4/1999 Kaiser
5,891,071 A 4/1999 Stearns et al.
5,900,303 A 5/1999 Billarant
5,916,187 A 6/1999 Brill
5,948,707 A 9/1999 Crawley et al.
5,971,946 A 10/1999 Quinn et al.
6,010,474 A 1/2000 Wycoki
6,021,780 A 2/2000 Darby
6,022,617 A 2/2000 Calkins
6,024,712 A 2/2000 Iglesias et al.
6,063,048 A 5/2000 Bodenschatz et al.
6,066,110 A 5/2000 Nauert
6,110,138 A 8/2000 Shirley
6,111,138 A 8/2000 Van et al.
6,142,965 A 11/2000 Mathewson
6,152,893 A 11/2000 Pigg et al.
6,159,583 A 12/2000 Calkins
6,250,651 B1 6/2001 Reuss et al.
6,254,554 B1 7/2001 Turtzo
6,267,741 B1 7/2001 Lerman
RE37,338 E 8/2001 McVicker
6,287,268 B1 9/2001 Gilmour
6,289,558 B1 9/2001 Hammerslag
6,360,404 B1 3/2002 Mudge et al.
6,368,295 B1 4/2002 Lerman
6,402,713 B1 6/2002 Doyle
6,405,731 B1 6/2002 Chiang
6,413,232 B1 7/2002 Townsend et al.
6,416,074 B1 7/2002 Maravetz et al.
6,461,318 B2 10/2002 Freeman et al.
6,485,776 B2 11/2002 Janusson et al.
6,520,926 B2 2/2003 Hall
6,540,703 B1 4/2003 Max
6,540,709 B1 4/2003 Smits
6,543,158 B2 4/2003 Dieckhaus
D477,409 S 7/2003 Mills et al.
6,592,538 B1 7/2003 Hotchkiss et al.
6,592,539 B1 7/2003 Einarsson et al.
6,596,371 B1 7/2003 Billarant et al.
6,598,250 B1 7/2003 Pekar
6,656,142 B1 12/2003 Lee
6,666,894 B2 12/2003 Perkins et al.
6,689,080 B2 2/2004 Castillo
6,726,641 B2 4/2004 Chiang et al.
6,735,819 B2 5/2004 Iverson et al.
6,740,054 B2 5/2004 Stearns
6,769,155 B2 8/2004 Hess et al.
6,773,411 B1 8/2004 Alvarez
6,861,371 B2 3/2005 Kamikawa et al.
6,861,379 B1 3/2005 Blaszczykiewicz
6,898,804 B2 5/2005 Sandler
6,898,826 B2 5/2005 Draper et al.
6,936,020 B2 8/2005 Davis
D519,637 S 4/2006 Nordt et al.
D519,638 S 4/2006 Nordt et al.
7,025,738 B2 4/2006 Hall
D520,141 S 5/2006 Nordt et al.
D521,644 S 5/2006 Nordt et al.
7,037,287 B2 5/2006 Cormier et al.
7,150,721 B2 12/2006 Houser
7,161,056 B2 1/2007 Gudnason et al.
7,169,720 B2 1/2007 Etchells et al.
7,198,610 B2 4/2007 Ingimundarson et al.
7,201,728 B2 4/2007 Sterling
7,303,539 B2 12/2007 Binder et al.
7,367,958 B2 5/2008 McBean et al.
7,448,115 B2 11/2008 Howell et al.
7,698,909 B2 4/2010 Hannula et al.
7,749,183 B2 7/2010 Ingimundarson et al.
7,762,973 B2 7/2010 Einarsson et al.
7,806,842 B2 10/2010 Stevenson et al.
7,874,996 B2 1/2011 Weinstein et al.
7,905,851 B1 3/2011 Bledsoe
7,937,973 B2 5/2011 Sorensen et al.
8,043,244 B2 10/2011 Einarsson et al.
8,277,401 B2 10/2012 Hammerslag et al.
8,328,747 B2 12/2012 Matsunaga
8,556,783 B1 10/2013 Ihli et al.
9,265,644 B2 2/2016 Einarsson et al.
9,358,146 B2 6/2016 Thorsteinsdottir et al.
9,364,365 B2 6/2016 Omarsson et al.
2001/0020143 A1 9/2001 Stark et al.
2001/0056251 A1 12/2001 Peters
2002/0032397 A1 3/2002 Coligado
2002/0077574 A1 6/2002 Gildersleeve et al.
2002/0082542 A1 6/2002 Hall
2002/0095750 A1 7/2002 Hammerslag
2002/0107464 A1 8/2002 Castillo
2002/0132086 A1 9/2002 Su-Tuan
2003/0032907 A1 2/2003 Prahl
2003/0069531 A1 4/2003 Hall
2003/0204156 A1 10/2003 Nelson et al.
2004/0002674 A1 1/2004 Sterling
2004/0054311 A1 3/2004 Sterling
2004/0058102 A1 3/2004 Baychar
2004/0137178 A1 7/2004 Janusson et al.
2004/0137192 A1 7/2004 McVicker
2004/0153016 A1 8/2004 Salmon et al.
2004/0176715 A1 9/2004 Nelson
2004/0199095 A1 10/2004 Frangi
2004/0225245 A1 11/2004 Nelson
2004/0267179 A1 12/2004 Lerman
2005/0020951 A1 1/2005 Gaylord et al.
2005/0038367 A1 2/2005 McCormick et al.
2005/0081339 A1 4/2005 Sakabayashi
2005/0159691 A1 7/2005 Turrini et al.
2005/0160627 A1 7/2005 Dalgaard et al.
2006/0015980 A1 1/2006 Nordt et al.
2006/0020237 A1 1/2006 Nordt et al.
2006/0026732 A1 2/2006 Nordt et al.
2006/0026733 A1 2/2006 Nordt et al.
2006/0026736 A1 2/2006 Nordt et al.
2006/0030802 A1 2/2006 Nordt et al.
2006/0030803 A1 2/2006 Nordt et al.
2006/0030804 A1 2/2006 Nordt et al.
2006/0030805 A1 2/2006 Nordt et al.
2006/0030806 A1 2/2006 Nordt et al.
2006/0070164 A1 4/2006 Nordt et al.
2006/0070165 A1 4/2006 Nordt et al.
2006/0084899 A1 4/2006 Verkade et al.
2006/0090806 A1 5/2006 Friedline et al.
2006/0094999 A1 5/2006 Cropper
2006/0116619 A1 6/2006 Weinstein et al.
2006/0135900 A1 6/2006 Ingimundarson et al.
2006/0135901 A1 * 6/2006 Ingimundarson ..... A61F 5/0123
602/26
2006/0135902 A1 6/2006 Ingimundarson et al.
2006/0135903 A1 6/2006 Ingimundarson et al.
2006/0155229 A1 7/2006 Ceriani et al.
2006/0156517 A1 7/2006 Hammerslag et al.
2006/0191110 A1 8/2006 Howell et al.
2006/0265845 A1 11/2006 Saderholm et al.
2007/0083136 A1 4/2007 Einarsson
2007/0106191 A1 5/2007 Mueller et al.
2007/0130665 A1 6/2007 Wang
2007/0167892 A1 7/2007 Gramza et al.
2007/0167895 A1 7/2007 Gramza et al.
2007/0185425 A1 8/2007 Einarsson et al.
2007/0225630 A1 9/2007 Wyatt et al.
2007/0225824 A1 9/2007 Einarsson
2008/0034459 A1 2/2008 Nordt et al.
2008/0066272 A1 3/2008 Hammerslag et al.
2008/0195014 A1 8/2008 Ingimundarson et al.
2008/0208095 A1 8/2008 Kazmierczak et al.
2008/0229556 A1 9/2008 Hammer
2008/0294079 A1 11/2008 Sterling et al.
2009/0099562 A1 4/2009 Ingimudarson et al.

(56) References Cited

U.S. PATENT DOCUMENTS

| | | | |
|---|---|---|---|
| 2009/0126413 A1 | 5/2009 | Sorensen et al. | |
| 2009/0216166 A1 | 8/2009 | Herzberg | |
| 2009/0259154 A1 | 10/2009 | Nace | |
| 2010/0068464 A1 | 3/2010 | Meyer | |
| 2010/0125231 A1 | 5/2010 | Knecht | |
| 2010/0268243 A1 | 10/2010 | Parker | |
| 2011/0057466 A1 | 3/2011 | Sachee et al. | |
| 2011/0112452 A1 | 5/2011 | Schiff | |
| 2011/0146032 A1 | 6/2011 | Hu et al. | |
| 2011/0275970 A1 | 11/2011 | Paulos et al. | |
| 2012/0010547 A1 | 1/2012 | Hinds | |
| 2012/0046585 A1 | 2/2012 | Lee et al. | |
| 2012/0090624 A1 | 4/2012 | Chang | |
| 2012/0109031 A1 | 5/2012 | Vollbrecht et al. | |
| 2012/0220910 A1 | 8/2012 | Gaylord et al. | |
| 2013/0184628 A1 | 7/2013 | Ingimundarson et al. | |
| 2013/0245523 A1 | 9/2013 | Romo | |
| 2014/0121579 A1 | 5/2014 | Hinds | |
| 2014/0194801 A1* | 7/2014 | Thorsteinsdottir ... | A61F 5/0102 602/26 |
| 2014/0214016 A1* | 7/2014 | Ingimundarson ..... | A61F 5/0125 606/16 |
| 2014/0221891 A1 | 8/2014 | Sreeramagiri et al. | |
| 2014/0257158 A1* | 9/2014 | Lee .................... | A44B 11/2584 602/12 |
| 2015/0005685 A1 | 1/2015 | Chetlapalli et al. | |
| 2015/0290014 A1 | 10/2015 | Anglada et al. | |
| 2016/0008157 A1 | 1/2016 | Brookover et al. | |
| 2017/0297278 A1 | 10/2017 | Lecursi et al. | |
| 2019/0029862 A1 | 1/2019 | Chavez-Taniwangsa et al. | |
| 2019/0314542 A1 | 10/2019 | Ish Cassit | |

FOREIGN PATENT DOCUMENTS

| | | | |
|---|---|---|---|
| DE | 10004561 | A1 | 8/2001 |
| DE | 202004012892 | U1 | 10/2004 |
| EP | 0050769 | A1 | 5/1982 |
| EP | 0196204 | A2 | 10/1986 |
| EP | 0611069 | A1 | 8/1994 |
| EP | 1016351 | A1 | 7/2000 |
| EP | 2612624 | A1 | 7/2013 |
| EP | 2612626 | A2 | 7/2013 |
| FR | 2399811 | A1 | 3/1979 |
| FR | 2553996 | A1 | 5/1985 |
| FR | 2766359 | A1 | 1/1999 |
| GB | 1209413 | A | 10/1970 |
| GB | 2136294 | A | 9/1984 |
| GB | 2455972 | A | 7/2009 |
| WO | 88/01855 | A1 | 3/1988 |
| WO | 94/00082 | A1 | 1/1994 |
| WO | 00/49982 | A1 | 8/2000 |
| WO | 00/70984 | A1 | 11/2000 |
| WO | 2006/015599 | A1 | 2/2006 |
| WO | 2006/069221 | A2 | 6/2006 |
| WO | 2006/069222 | A2 | 6/2006 |
| WO | 2008/115376 | A1 | 9/2008 |
| WO | 2009/052031 | A1 | 4/2009 |
| WO | 2010/117749 | A2 | 10/2010 |
| WO | 2011/073803 | A2 | 6/2011 |

OTHER PUBLICATIONS

"Velstick semi-rigid Fastener Furnished in Separate, Mating Components", Velcro Fasteners, Spaenaur, Sep. 2, 2009, 1 Page.

Advertisement: "Axiom", 3 pages, Bledsoe by Medical Technology, Inc. (visited Jun. 15, 2005), http://www.bledsoebrace.com/custom/axiom.asp.

Advertisement: "Bellacure: The Treatment Device", 6 pages, Bellacure, Inc. (visited Jan. 5, 2006), http://www.bellacure.com/products/index/html.

Advertisement: "Custom Engineered Fabrics and Products for Advanced High Performance", 1 page, Gehring Textiles (visited Dec. 15, 2005), http://www.gehringtextiles.com/d3.html.

Advertisement: "Lerman 3-Point Knee Orthosis", 2 pages, Becker Orthopedic of Troy, MI (visited Feb. 26, 2006), http://www.beckerortho.com/knee/3-point/htm.

Advertisement: "M2 Inc. Parts Catalog", 3 pages, M2 Inc. of Winooski, VT (visited Mar. 29, 2005), http://www.m2intl.com/medical.MedClsr.htm.

Advertisement: "McDavid Knee Guard and 155 Ligament Augmentation System", 3 pages, Advanced Brace of Irving TX (visited Mar. 8, 2005), http://www.supports4u.com/mcdavid/kneeguard.htm.

Advertisement: "Triax", 1 page, Lanxess AG (visited Mar. 8, 2005), http://www.techcenter.lanxess.com/sty/emea/en/products/description/57/index/jsp?print=true&pid=57.

Advertising Brochure: "Anderson Knee Stabler", 4 pages, Omni Scientific, Inc. of Lafayette, CA. Feb. 7, 2013.

Advertising Brochure: "Freedom to Perform-Fusion", 5 pages, (2005).

Advertising Brochure: "Fusion XT", 2 pages, Breg, Inc. of Vista, CA (2005).

Advertising Brochure: "Fusion", 6 pages, Breg, Inc. of Vista, CA (2005).

Advertising Brochure: "Gli Unloader Select", 2 pagse, Ossur HF of Reykjavik, Iceland (visited Mar. 8, 2005), http://www.ossur.com/pring.asp?pageID=1729.

Advertising Brochure: "Lerman Multi-Ligaments Knee Control Orthosis", 2 pages, Zinco Industries, Inc. of Montrose, CA (1985).

Advertising Brochure: "NUKO Camp", 6 pages, Camp International, Inc. Jackson, MI (1984).

Advertising Brochure: "OTI Brace", 4 pages, Orthopedic Technology, Inc. of San Leandro, CA. Feb. 7, 2013.

Advertising Brochure: "The 9 Innovations of the Axiom Custom Brace", 1 page, Bledsoe, Medical Technology, Inc. (2005).

Advertising Brochure: "The Four Axioms of Functional Bracing", 2 pages, Bledsoe by Medical Technology, Inc. (2005).

Advertising Brochure: "The Leader in Knee Motion Management," 8 pages. Donjoy, Carsbad, CA. Feb. 7, 2013.

Advertising Brochure: "The Lenox Hill Lightweight", 1page, Lenox Hill Brace, Inc., New York, NY. Feb. 7, 2013.

Advertising Brochure: "XCL System", 2 pages, Innovation Sports of Foothill Ranch, CA. Feb. 7, 2013.

Article: "An Orthosis for Medial or Lateral Stabilization of Arthritic Knees", by S. Cousins and James Foort, Orthotics and Prosthetics, vol. 29, No. 4, pp. 21-26, Dec. 1975.

Article: "Osteoarthritis of the Knee: An Information Booklet", Arthritis Research Campaign (visited Dec. 14, 2004) http://www.arc.org.uk/about_arth/booklets/6027/6027.htm.

Article: "Thermoplastic Elastomers TPE, TPR, TPV", 6 pages (visited Mar. 14, 2007), http://www.bpf.co.uk.bpfindustry/plastics_thermplasrubber_TBR.cfm.

Reference: "Anatomical Planes", 1 page, (visited Mar. 26, 2005), http://www.spineuniverse.com/displayarticle.phpo/article1023.html.

Technical Manual: Bellacure: Restore Your Lifestyle, 10 pages, Bellacure, Inc. (2005).

Technical Manual: "Boa Technology", 3 pages, Boa Technology, Inc. of Steamboat Springs, CO, Feb. 7, 2013.

International Search Report from PCT Application No. PCT/US2018/054820, Feb. 8, 2019.

* cited by examiner

FIG. 5A
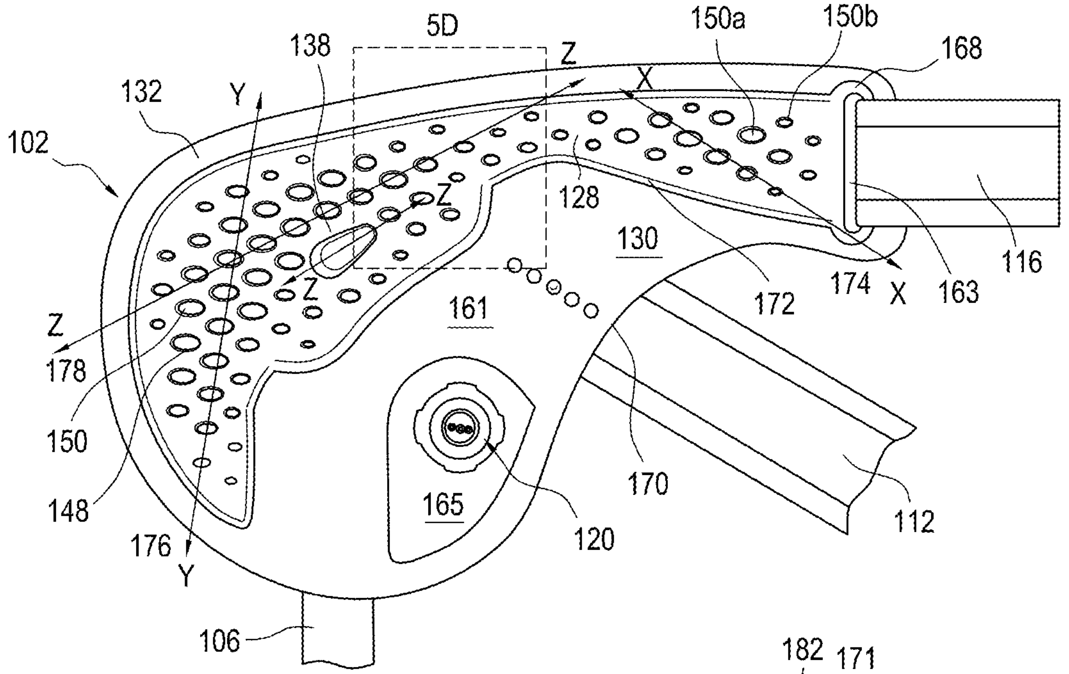
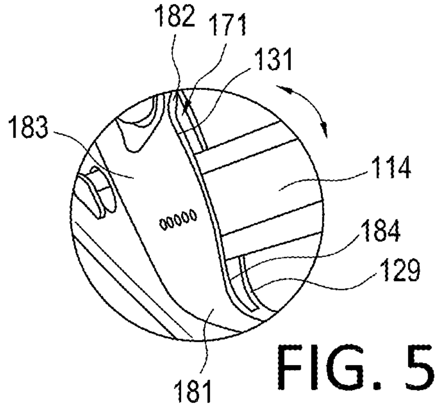
FIG. 5C
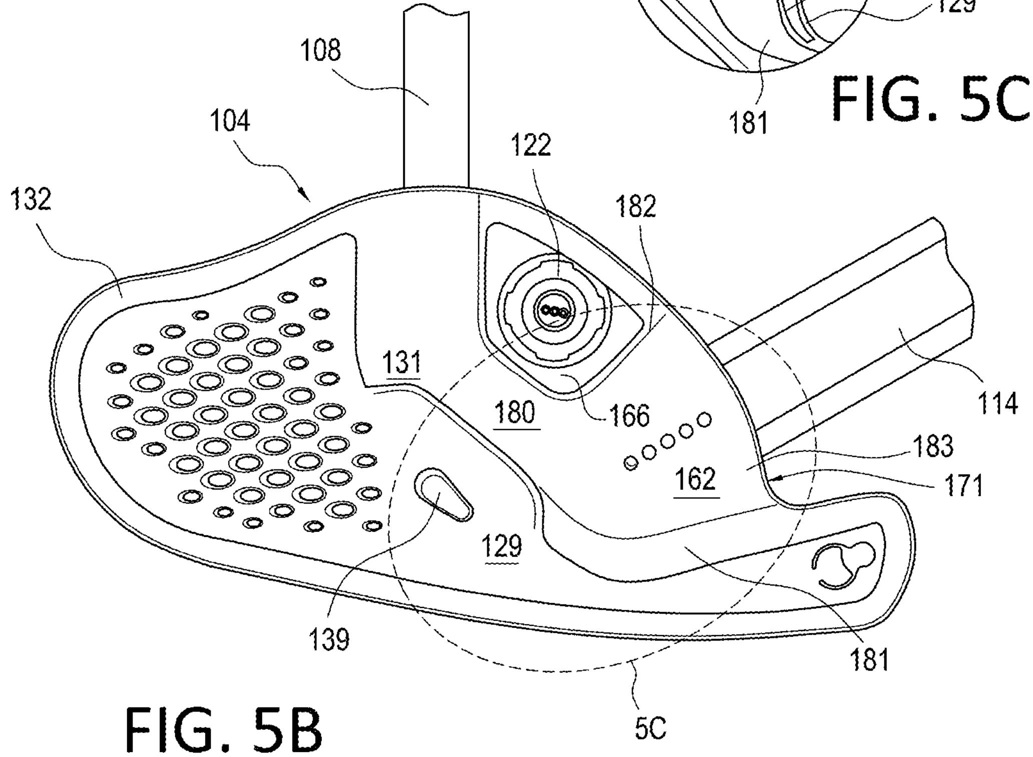
FIG. 5B

CONNECTOR FOR AN ORTHOPEDIC DEVICE

FIELD OF THE DISCLOSURE

The present disclosure relates to an orthopedic device, and more particularly to an orthopedic device that provides stability, protection, support, rehabilitation, and/or unloading to a portion of the human anatomy in a streamlined, comfortable, and light manner.

BACKGROUND

Known orthopedic devices are used for providing stability, protection, support, rehabilitation and/or unloading of a portion of the human anatomy. These known devices, however, are often considered as being uncomfortable, physically bulky, heavy, not durable, tedious and/or difficult to adjust, and costly, requiring numerous manufacturing processes to be produced.

An example of an orthopedic device is a knee brace. Knee braces are widely used to treat many knee infirmities. Such braces may be configured to impart forces or leverage on the limbs surrounding the knee joint to relieve compressive forces within a portion of the knee joint, or to reduce the load on that portion of the knee. If knee ligaments are weak and infirm, a knee brace may stabilize, protect, support, unload, and/or rehabilitate the knee.

The knee is acknowledged as one of the weakest joints in the body and serves as the articulating joint between the thigh and calf muscle groups. The knee is held together primarily by small but powerful ligaments. A healthy knee has an even distribution of pressure in both its medial and lateral compartments. It is normal for a person with a healthy knee to place a *varus* moment on the knee when standing so pressure between the medial and lateral compartments is uneven but still natural.

Knee instability arising out of cartilage damage, ligament strain, and other causes is relatively commonplace since the knee joint is subjected to significant loads during almost any physical activity requiring legs.

Compartmental osteoarthritis is a problematic knee infirmity. It may arise when there is a persistent uneven distribution of pressure in one of the medial and lateral compartments of the knee. Compartmental osteoarthritis can be caused by injury, obesity, misalignment of the knee, or due to aging of the knee. A major problem resulting from osteoarthritis is that smooth cartilage lining the inside of the knee wears away. This leads to a narrowing of the joint space leading to the development of cysts and erosions in the bone ends. Because of the narrowing of the joint, bone comes directly in contact with bone, and an uneven distribution of pressure develops across the knee, which may cause the formation of bone spurs around the joint. These changes ultimately lead to increasing pain and stiffness of the joint.

While there are no cures to osteoarthritis, there are many treatments. Individuals with a diagnosis of isolated lateral or medial compartmental osteoarthritis of the knee are confronted with many treatment options such as medications, surgery, and nonsurgical interventions. Nonsurgical interventions include using canes, lateral shoe wedges, and knee braces.

Meniscal tears, or tears in the meniscus, are another common knee ailment that impede proper knee function. These meniscal tears are frequently remedied through partial meniscectomy, which is one of the most common orthopedic procedures in the U.S. as about ⅓ of men older than 50 have asymptomatic meniscal tears. Acute tears may be treated conservatively, and recent evidence suggests that surgery, including partial meniscectomy, may be unnecessary for degenerative tears. Non-surgical treatment of meniscal tears may involve a period of non/reduced weight bearing.

Degenerative tears are often associated with osteoarthritis changes in the knee. Osteoarthritis and degenerative meniscal tears share many of the same risk factors and biological processes. It may be difficult to ascertain if one condition precedes the other, or whether they occur independently or simultaneously.

Knee bracing is useful in providing compartment pain relief resulting from the above-mentioned pathologies of osteoarthritis and/or meniscal tears by reducing the load on the injured meniscus or tear, and/or knee compartment through applying an opposing external valgus or *varus* moment about the knee joint. Unloading knee braces have been shown to significantly reduce osteoarthritis knee pain while improving knee function. While known knee braces succeed at reducing pain or at stabilizing a knee joint, many users find these braces to be bulky, difficult to don, complicated to configure and/or adjust, not durable, and uncomfortable to wear.

Orthopedic device frames may cause pressure points, be uncomfortable around the edge, have poor breathability, look and feel bulky and/or aesthetically unattractive, be difficult to adjust in shape, and lack durability, among other problems. Attachments on a frame of an orthopedic device can cause the orthopedic device to be unsightly, difficult to use compliantly (such as by catching on or not fitting with clothing or other objects) and may lead to maintenance costs and issues as attached components become detached.

Strapping systems are commonly used to secure orthopedic devices to the user's anatomy. Few changes have been made to strapping systems, and little focus has been given to improving strapping. Rather, the emphasis in orthopedic devices often relates to the frame structure and methods for preventing migration of the orthopedic device on the user during use, and strapping systems are typically off-the-shelf products, with little to no focus devoted thereto.

Current strap designs typically involve aggressive hook and loop systems with a tendency to tear soft-good type braces or make it difficult for corresponding areas on a hard frame to maintain hook or loop patches for receiving straps bearing corresponding locking hook or loop. These straps may have a single property regarding elasticity; they are elastic or inelastic, but rarely do they include both elasticities arranged at strategic locations.

Sizing of many current strap designs may allow for severing the length of the strap to fit a user's anatomy at a time, but such strap designs often lack means for lengthening or reducing length, as desired by a user or set by a clinician. Current strap designs do not possess means for quickly attaching and removing the strap systems from a frame of the orthopedic device. As the strap systems are often not given much design consideration, they cause complaints due to discomfort and difficulty of adjustment. They may be formed from nylon or other inexpensive textile materials lacking sufficient pressure distribution or breathability. Such materials can also lack desired durability. There is a need for strap systems that are injection molded and free of textiles.

Current straps also lack designs and/or implements to improve durability of the strap itself. Hook and loop fasteners are commonly used for adjusting strap length but can wear out, causing durability issues. Hook and loop fasteners have the additional disadvantage of frequently coming undone during normal use and being imprecise to adjust, making it difficult to ensure a sure and precise fit, especially for users with limited dexterity or cognition.

Strap systems and frames may be designed in a way that allows migration of one or more straps along a user's anatomy during use, which migration further adds to discomfort, poor fit, and difficulty of adjustment. Straps may further apply forces or pressure along narrow, localized areas of a user's body, leading to discomfort especially during long durations of use.

Orthopedic frames and strap systems may be adjustable in size by various means such as by tensioning a cable, but a problem is that the adjustment systems add bulk and discomfort to the device. Attachments and structures for routing tensioning cables may protrude from one or more shells of the frame, adding bulk, reducing comfort, and reducing durability as the protruding attachments and structures for routing the cables may be more prone to breaking or malfunctioning and add bulk. There may be too few of such attachments and structures to route the cable, leading to uneven tensioning and/or discomfort including poor fit. Adjustment systems, such as dial tensioners, may contribute to migration of the frame against the user as the adjustment system is actuated. Cables that terminate on straps rather than within the dial tensioner may reduce durability by causing maintenance problems; for example, the straps may more easily become detached from the frame, necessitating repairs or replacements of components.

Comfort, cost, and durability are of concern in orthopedic devices for osteoarthritic treatment because often the orthopedic device must be worn for long periods of time and for significant lengths of the user's life. For instance, surgery and knee replacement may be avoided or deferred for patients who diligently use an osteoarthritic knee brace, but this means the brace must be comfortable and simple enough to don, use, and doff regularly. There is a need for a knee brace with components that are both durable and low profile to minimize bulk, and easy to use but reliably functional.

There is need of an orthopedic device suitable for treating osteoarthritis and/or meniscal tears, reducing knee pain, improving knee function, reducing compartmental knee loads, and offering ease of application and adjustment while overcoming the problems of existing braces.

SUMMARY

The exemplary embodiments have streamlined features capable of providing relief for degenerative meniscal tears and/or medial or lateral compartmental osteoarthritis, or providing functional stability of the knee, without the attendant drawbacks of known unloading knee braces. The concepts described with the exemplary knee brace embodiments may be extended to many wearable devices configured to be secured to and/or support numerous portions of anatomy. The embodiments are aimed at improving the life and mobility of affected users by reducing knee pain, improving knee function, reducing compartmental knee loads, and offering ease of application and adjustment while improving durability and reducing bulk, cost, and complexity.

According to the exemplary embodiments, the orthopedic device has an improved strap connection including a buckle assembly and a strap interface. The dynamic force straps and thigh or calf straps can be released by opening a single buckle, which mitigates a need to readjust a tensioning mechanism, easing donning and doffing. The strap connection has a compliant structure better yielding to the anatomy of the wearer of the orthopedic device and integrates the straps with the strap connection to streamline the size of the strap connection while improving comfort and durability.

In embodiments of the disclosure, the strap connection is arranged to improve comfort and durability by providing a single connection on a buckle assembly that connects to two straps, such as one dynamic force strap and one calf or thigh strap, but with sufficient flexibility that the straps may bend in response to the contours of the orthopedic device or the user's leg.

For instance, the buckle assembly may define a rigid base part that attaches the straps to the buckle assembly and which is integrally formed with a softer overmolded portion that transitions via a widened profile to two independently flexible strap mount parts. The strap mount parts may correspond to an individual strap and may comprise a soft, flexible overmolded material integrally formed and interlocks with a textile material of the straps. This arrangement provides that the straps may bend and flex via the strap mount parts to maintain a slim profile and to optimally conform to the user's dimensions without losing their robust connection to the buckle assembly.

In an embodiment, from a central axis of the buckle assembly the strap mounts may rotate outwardly or inwardly relative to one another, bringing the straps closer together or farther apart; the strap mounts may also bend inwardly for close engagement of the straps against the user, evenly distributing pressure over the user's leg and minimizing bulk of the orthopedic device. The strap mounts may be configured with patterns of apertures or tapered sections for bending and rotating in desired directions.

The tensioning mechanism is integrated with shells of the frame of the orthopedic device to reduce cable lengths of the tensioning mechanism, and the bulk of the straps. The tensioning mechanism is more stably and durably secured to the orthopedic device by rather being on the more rigid shells, as opposed to being on the dynamic force straps.

The overall strapping configuration of the orthopedic device is simplified to avoid material on the body of the wearer, particularly in the popliteal region. The straps are configured to avoid stretching out. The straps are further provided with color or material distinction to better aid the user in knowing which straps to apply during donning and doffing and where to apply the straps. The straps, particularly calf and thigh straps, may have different properties relative to one another, such as elasticity and inelasticity, which may reduce migration preventing the straps and hence the orthopedic device from slipping down a leg and hindering compliant use of the orthopedic device.

The strap durability is improved by adding more rigidity to the dynamic force straps by a rigid webbing to avoid stretching after an initial fitting. The interface with the strap connection provides flexibility by incorporating different degrees of flexibility in the strap connection itself, and by making the flexibility at the connector commensurate with the dynamic force straps and the thigh and calf straps.

The orthopedic device may further utilize sleeves in desired areas for additional reinforcement of the device against the limb of a user with even pressure distribution, for enhanced proprioception, and to maintain the device in a desired configuration. For instance, a sleeve may be removably attached at the dynamic force straps and configured to extend over a side portion or a rear/popliteal portion of a user's leg, reducing pressure points applied by the straps, especially the dynamic force straps which unload the joint and may exert an uncomfortable force against localized portions of the leg, and distributing pressure evenly to enhance proprioception and consequently comfortable use of the orthopedic device.

The shells of the frame of the orthopedic device are configured with a contour that is smaller than in known prior art devices and are adapted to avoid pressure points on the calf and other regions of the user's leg. The shells have peripheral edges created by overmolding a more flexible material which forms the flexible edges over the rigid or semi-rigid shells. The softer and more flexible material of the peripheral edges extends over the shells to create functional areas with better traction or fit compared to the rigid or semi-rigid material of the shells. The padding underlying the shells and arranged adjacent the user is arranged to be flush with the peripheral edges so that the padding need not overextend beyond the peripheral edges and reduces overall bulk of the orthopedic device.

These advantageous features of the shells of the orthopedic device may be provided by adding overmolded overlays on the shells, the overlay extending over the shells and defining features useful for attaching, securing, tensioning, and or flexing straps or other attachments such as tensioning devices while maintaining a soft feel and a minimized profile. In contrast to many existing devices which add components like straps, tensioning devices, and liners directly to the shells of the frame, the overmolded overlays of embodiments of the disclosure advantageously define features such as clearances that may receive therein components like straps or tensioning devices and thereby secure the components to the frame and maintain a sleek, minimized, aesthetically pleasing, and comfortable profile, without the disadvantages of bulky attachment elements which increase bulk and maintenance issues of the device.

The exemplary embodiments also include various strap systems that provide versatility in sizing of length, quick and efficient attachment to the frame of the orthopedic device, enhanced durability, improved fit, and enhanced comfort over known strap systems in orthopedic devices.

BRIEF DESCRIPTION OF THE DRAWINGS

These and other features of the present disclosure will become better understood regarding the following description, appended claims, and accompanying drawings.

FIG. 5A is an elevational schematic view of a first shell in the orthopedic device of FIGS. 1A and 1B.

FIG. 5B is an elevational schematic view of a second shell in the orthopedic device of FIGS. 1A and 1B.

FIG. 5C is a detail view from FIG. 5B.

Figure 1A:
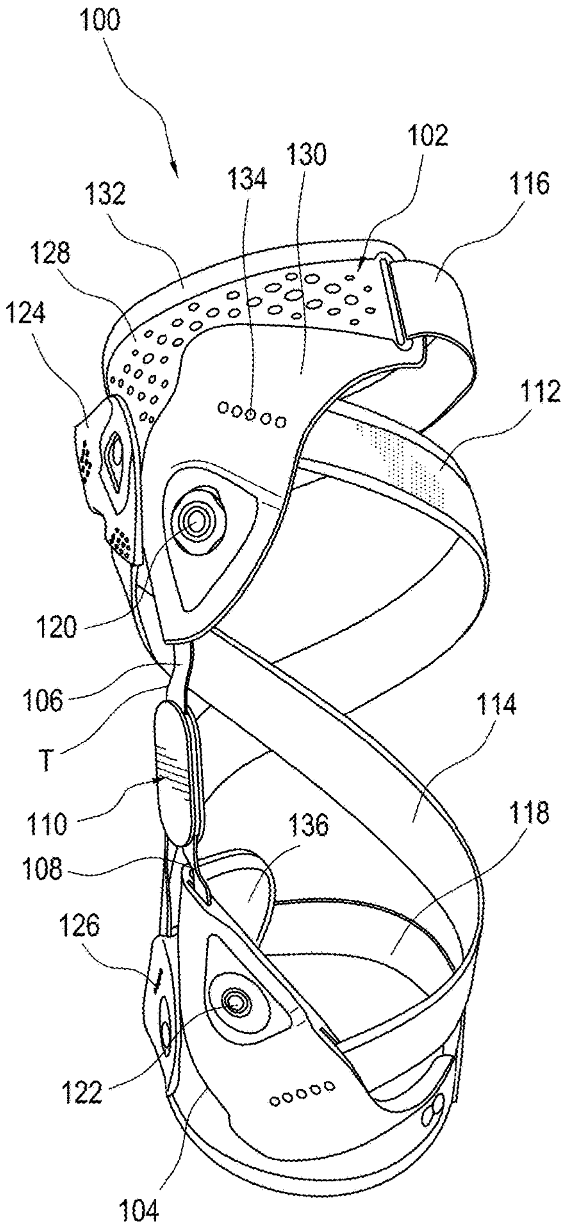
FIG. 1A is a side elevational view of an orthopedic device.

The drawing figures are not necessarily drawn to scale, but instead are drawn to provide a better understanding of the components, and are not intended to be limiting in scope, but to provide exemplary illustrations. The figures illustrate exemplary configurations of an orthopedic device, and in no way limit the structures or configurations of an orthopedic device and components according to the present disclosure.

DETAILED DESCRIPTION OF VARIOUS EMBODIMENTS

Figure 1B:
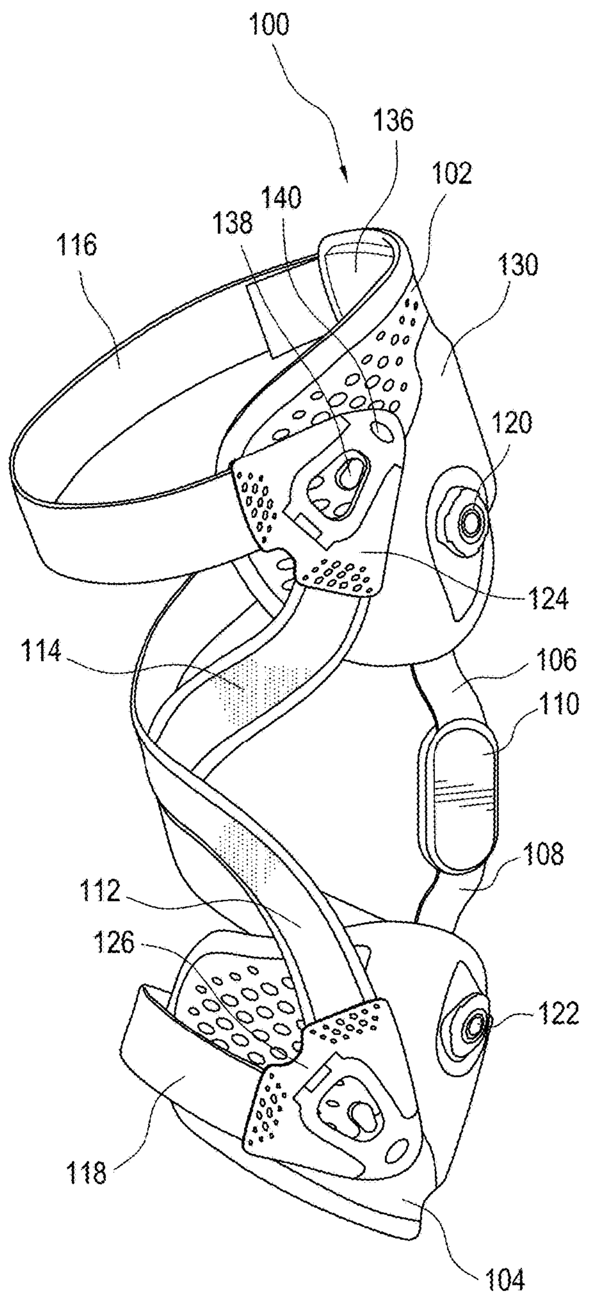
FIG. 1B is a front elevational view of the orthopedic device of FIG. 1A.

As shown in FIGS. 1A and 1B, the orthopedic device 100 is in the form of a knee brace, and builds on the basic description of a knee brace in U.S. Pat. No. 9,358,146, issued on Jun. 7, 2016, incorporated herein by reference. The orthopedic device 100 relates to and functions, at least in part, similarly to the orthopedic device discussed in U.S. Pat. No. 7,198,610, issued on Apr. 3, 2007, and incorporated herein by reference.

The embodiments of the orthopedic device 100 improve over known knee braces by providing easier donning/doffing, enhanced wearing comfort, sleeker fit, simpler and leaner strapping systems, improved anti-migration means and better resistance to wear and tear.

According to the depicted embodiment, the orthopedic device 100 includes a first shell 102, such as a thigh shell, a second shell 104, such as a calf shell, and a hinge 110 connecting to the first and second shells 102, 104 by first and second struts 106, 108. Either or both struts 106, 108 may be slightly twisted from at least more than 0 degrees to 15 degrees of normal (i.e., parallel to a sagittal or frontal plane), and preferably around 5 degrees. The twist T allows for a more anatomical fit and reduces rotation of the struts 106, 108 and hence the orthopedic device 100 on the leg of the user.

A first strap or dynamic force strap 112 has a first end slidably connecting to the first shell 102 and a second end removably anchoring to the second shell 104. An overlay 130 extends over a portion of the first and second shells 102, 104 and forms a clearance 184 (shown in FIG. 5C) with the first and second shells 102, 104 into which the first ends of the first dynamic force strap 112 and a second dynamic force strap 114 extend.

To reduce bulkiness of the orthopedic device 100, and to further provide a more stable platform for tensioning the dynamic force straps 112, 114, a cable connecting the dynamic force straps 112, 114 to a tensioning mechanism 120, 122, can be reduced in length by mounting tensioning mechanisms 120, 122 directly to the shells 102, 104 and confining the cable and the travel thereof within the shells 102, 104. The overlay 130 shields a portion of the dynamic force straps 112, 114, with the cable preferably concealed therein.

The first tensioning mechanism 120 is mounted directly onto the first shell 102 and is movable relative to the first shell 102, e.g. via a rotation, to incrementally adjust a length of the first dynamic force strap 112 between the first and second shells 102, 104. The overlay 130 defines indicia 134 indicating the length of the first dynamic force strap 112 between the first and second shells 102, 104. The second dynamic strap 114 likewise has a first end slidably connecting to the first shell 102, and a second end removably anchors to the second shell 104. The second tensioning mechanism 122 is mounted directly onto the second shell 104 and is movable relative to the second shell 104, e.g. via a rotation, to incrementally adjust a length of the second dynamic force strap 114 between the first and second shells 102, 104.

The first shell 102 defines a first shell body 128 and a peripheral edge 132 extending about the first shell body 128, such that the peripheral edge 132 is more flexible than the first shell body 128. The first shell body 128 is preferably rigid or semi-rigid. A liner 136 is located on an inner surface of the orthopedic device 100 and the first shell 102, has edges flush with the peripheral edge 132 so as not to extend beyond the periphery of the peripheral edge 132.

In known prior art devices, the strapping systems are cumbersome during adjustment over the leg of the user, which makes donning and doffing the orthopedic device difficult. According to the embodiments of the disclosure, the donning and doffing of the straps is streamlined so the thigh and calf straps are released by opening the brace with the dynamic force strap. Such an arrangement removes the necessity to readjust the tensioning mechanisms (which may be difficult to do precisely and repeatedly for many users) and requires less force to close or don the orthopedic device.

The orthopedic device 100 has a first circumferential strap 116 connecting to opposed sides of the first shell 102 to create a circumference with the first shell 102. The circumferential strap 116 has a first end securing to the first shell 102, and a second end releasably connecting to the first shell 102 by a first connector 124. The first connector 124 has first and second arms or strap mounts 190, 192 (shown in FIG. 2A), with the first arm 190 connecting to the second dynamic force strap 114 and the second arm 192 securing to the first circumferential strap 116. These first and second arms 190, 192 (shown in FIG. 2A) form a multi-directional strap mount, capable of directing at least two straps in two directions, respectively. Of course, these strap mount may form more than two arms, depending on an arrangement of straps. A second connector 126, analogous to the structure of the first connector 124, releasably connects a second end of second circumferential strap 118 and the first dynamic force strap to the second shell 104. Like the first circumferential strap 116, the first end of the second circumferential strap 118 may secure to the second shell 104.

Figure 2A:
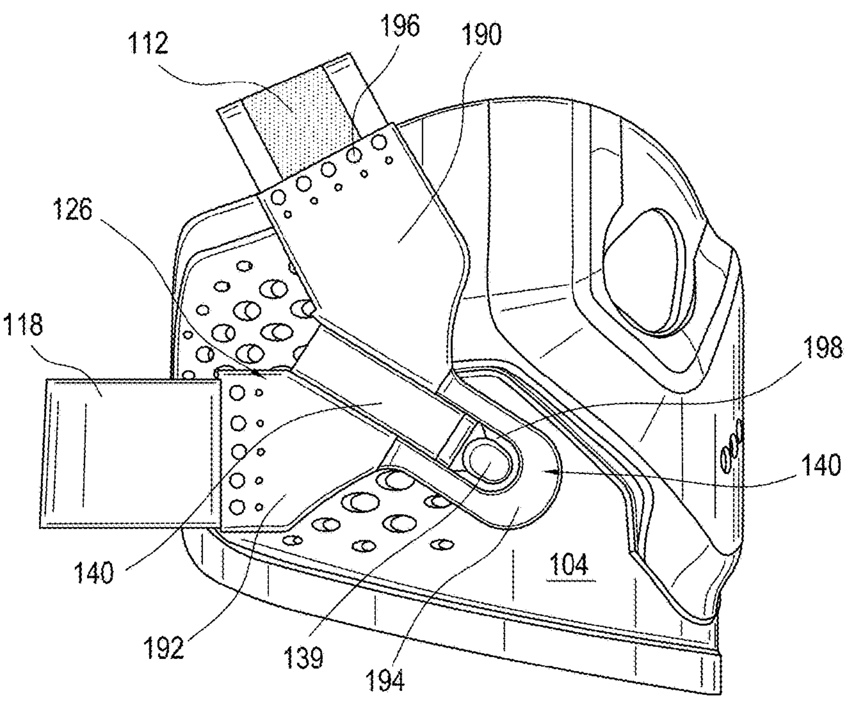
FIG. 2A is a schematic view of a connector in the orthopedic device of FIGS. 1A and 1B.

As shown in FIGS. 1A, 1B and 2A, the first connector 124 and the second connector 126 include a buckle assembly 140 releasably securing to the first or second shell 102, 104, respectively. The buckle assembly 140 defines a lever 194 having a seat 198 for releasably securing to a hook 138, 139 defined by the first shell 102. The first circumferential strap 116 is non-adjustably secured to the first connector 124 along a connection interface 196, with the second circumferential strap 118 likewise secured to the second connector 126 at a connection interface 196. The first and second circumferential straps 116, 118 may be elastic to prevent migration over the leg, and to tension about the user's leg due to both the inherent elasticity of the first and second circumferential straps 116, 118, and the tensioning thereof.

Figure 2B:
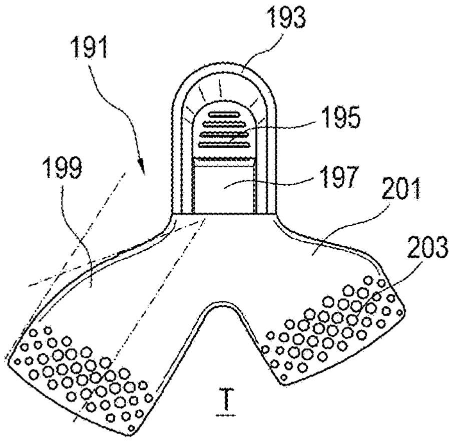
FIG. 2B is a front plan view of another embodiment of a connector.
Figure 2C:
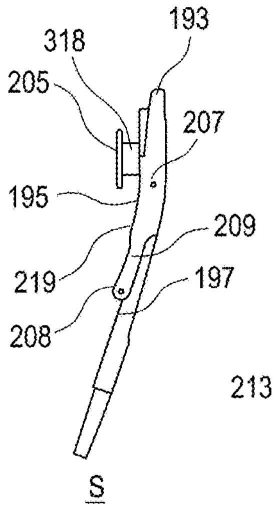
FIG. 2C is a side elevation view of the connector of FIG. 2B.
Figure 2D:
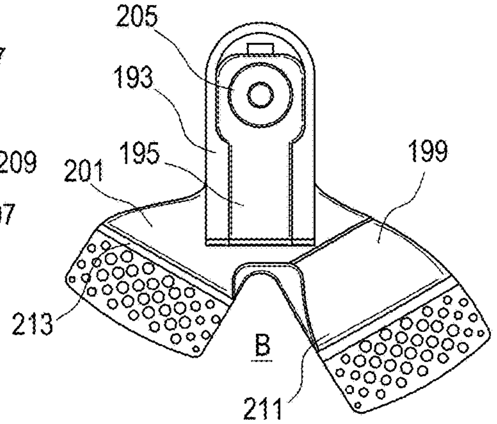
FIG. 2D is a rear plan view of the connector of FIG. 2B.

Referring to FIGS. 2B to 2D, another embodiment of a connector 191 is depicted bearing common components as in the first and second connectors 124, 126. The connector 191 has a lever 193 pivotally and lockingly connected at pivot point 207 to a base part 197. The lever 193 is also pivotally connected to a connecting part 195 at pivot point 208. The connector 191 is configured to have an open configuration in which the base part 197, the lever 193, and the connecting part 195 are spaced apart and connect only at the pivot points 207, 208, and a closed configuration in which the base part 197, the lever 193 and the connecting part 195 lay flush against one another.

The first and second arms 199, 201 extend from the base part 197, and define perforations 203 formed as part as the connection interface 211 with the straps. The perforations 203 reduce material of the arms 199, 201 and aid in increasing the flexibility of the arms 199, 201 so the end portions of the arms 199, 201 structurally flex generally commensurately with the flexibility of the straps. In this manner, there is a reduction or elimination of pressure points at the interface of the arms 199, 201 and the straps, particularly where the arms 199, 201 terminate, and the straps continue. The perforations may gradually increase in size and/or number toward to the end portions of the arms 199, 201, so the pressure points and flexibility is gradually increased as the straps terminate.

Contrary to the first and second connectors 124, 126 depicted in the embodiment of FIGS. 1A, 1B, and 2A, the connector 191 defines a locking part 205 adapted to fittingly secure to one of the first and second shells 102, 104 by and at an opening. The connecting part 195 has a portion 209 that extends underneath the base part 197, and may have a slightly curved profile 219 to accommodate, for example, the contour of a leg cross-section. The connecting part and lever 195, 193 preferably lock to one another, as shown in FIG. 2E.

Figure 2E:
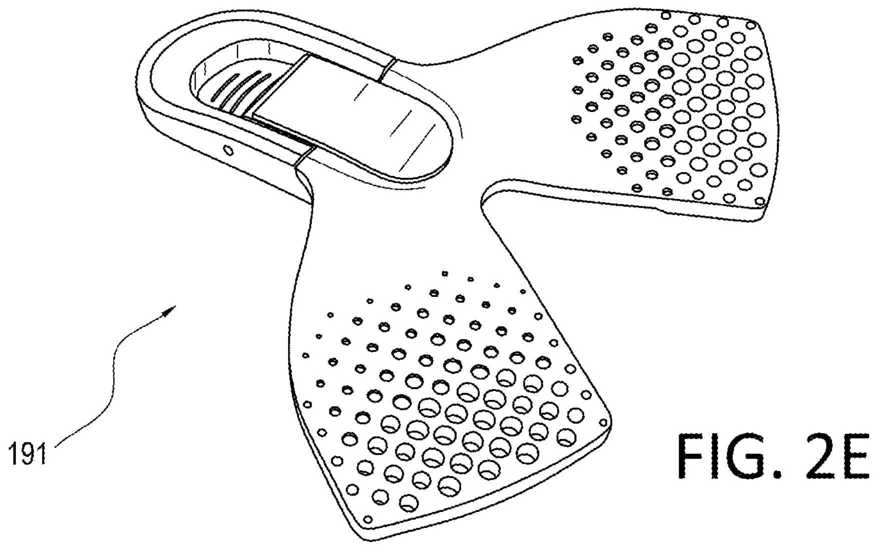
FIG. 2E is a perspective view of the connector of FIG. 2B in a closed configuration.
Figure 2F:
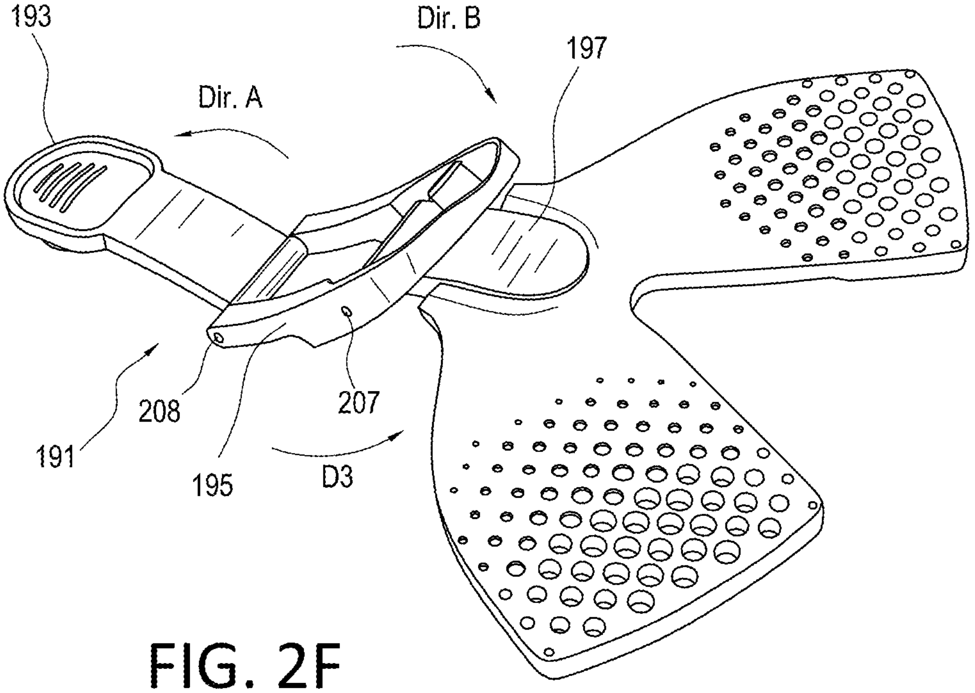
FIG. 2F is a perspective view of the connector of FIG. 2B in an open configuration.

The first and second arms 199, 201 are preferably flexible, whereas the base part 197 may be semi-rigid, as explained in more detail referring to FIG. 2F. To yet further facilitate flexibility of the first and second arms 199, 201, they may be provided with hinges 213 between the connection interface 211 and the base part 197. The hinges 213 preferably lend greater flexibility inwardly or toward the user as opposed to outwardly and away from the user, thereby facilitating a close, low-profile engagement between the components of the orthopedic device 100 and the user.

FIGS. 2E and 2F show the connector 191 in a closed configuration, as in FIG. 2E, and an open configuration, as in FIG. 2F. In the open configuration, an end of the connecting part 195 rotates at pivot point 208 in direction D1 away from the lever 193, which is pivotally secured to the base part 197 at pivot point 207, which rotates in direction D2 toward the base part 197. The base part 197 may rotate in direction D3 to create an open configuration relative to the lever 193.

Figure 2G:
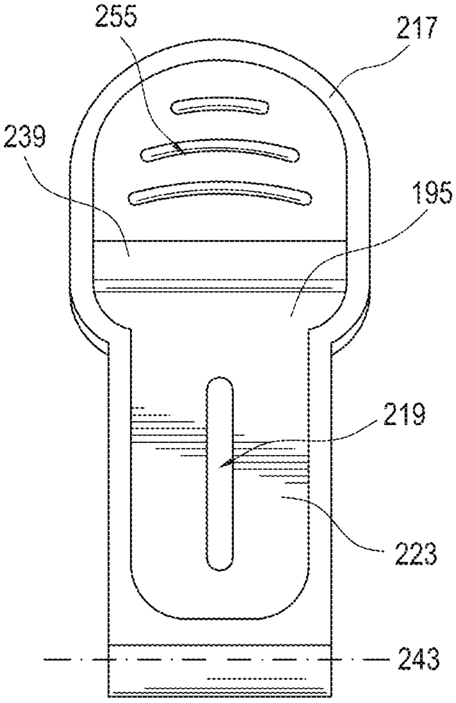
FIG. 2G is a plan view of an intermediate part in the connector of FIG. 2B.

FIG. 2G depicts a detail of the connecting part 195. The connecting part 195 preferably defines a grip 225 located at a forward end 217. The connecting part 195 defines a groove 239 into which a forward end 241 of the base part 197 rests. The connecting part 195 may define a marking 219 on an elongate portion 223 of the connecting part 195 exposed only when the connector 191 is open, and serves as an indicator of whether the connector 191 is closed. A rear end of the connecting part 195 has a channel 243 forming part of the pivot point 208 with the lever 193.

Figure 2H:
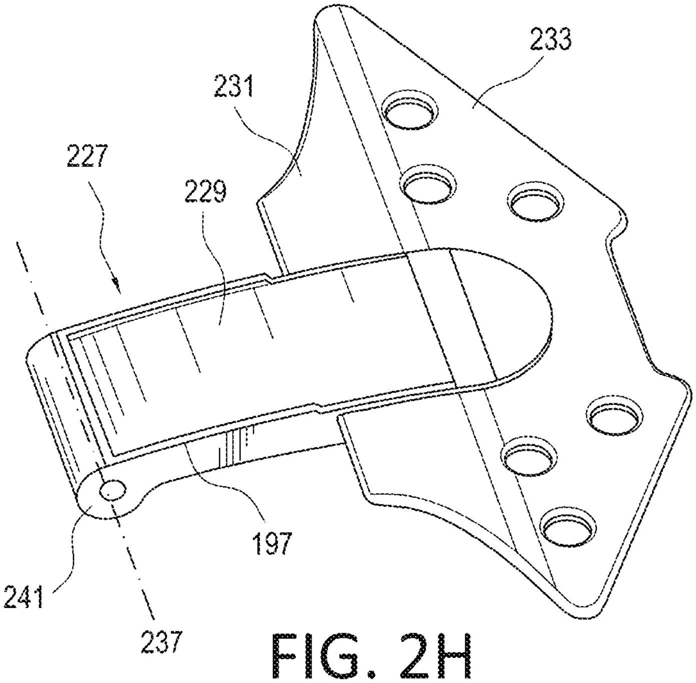
FIG. 2H is a perspective view of a reinforcement part in the connector of FIG. 2B.

FIG. 2H shows a reinforcement part 227 that supports the base part 197. The reinforcement part 227 is formed from a semi-rigid or rigid material, and is substantially more rigid than the flexible material forming the arms 199, 201. The base part 197 comprises an elongate section 229 that extends to a web portion 231 that serves in part to impart structure to at least part of the arms 199, 201. The web portion 231 is preferably flat and offers more flexibility than the base part 197 due to its generally flat profile. The elongate section 229 has a profile 233 adapted to partially correspond to shapes of the arms 199, 201. The elongate section 229 has the forward end 241 shaped for engaging the connecting part 195 at the groove 239, and defines a channel 237 forming part of the pivot point 207 between the lever 193 and the base part 197.

Figure 2I:
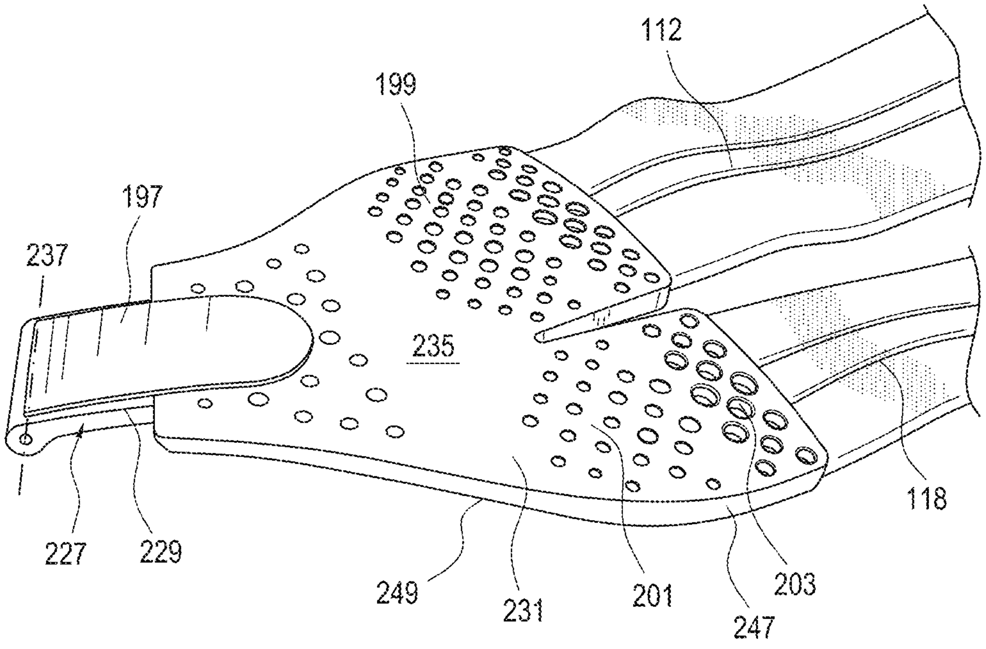
FIG. 2I is a perspective view of another embodiment of a connector.

FIG. 2I shows another embodiment of the connector which exemplifies how an overmold 235 is placed over the reinforcement part 227, and the material of the overmold 235 forms the arms 199, 201. The overmold 235 comprises more flexible material than the material forming the reinforcement part 227, and may have a softer touch due to a lower hardness. The ends of the straps 112, 118 are surrounded by the overmold 235 and integrally secured therewith due to interlocking of the material of the overmold 235 and/or shrinkage thereof with the material of the straps 112, 118. The rigid web portion 231 offers additional rigidity to the overmold 235, striking a balance with the flexibility of the overmold 235 and the greater rigidity of the reinforcement part 227.

An overmold in the context herein has its ordinary meaning of a first material, or substrate, that is partially or fully covered by subsequent materials (overmold materials) during the manufacturing process. In this embodiment, the reinforcement part 227 is molded over by the more pliant material of the overmold. The overmold 235, however, forms structural features of the arms 199, 201 whereby the reinforcement part 227 does not fully extend into the arms so as enable the arms to flexibly depend from the reinforcement part 227, thus better conforming to the needed shape of the device.

End portions of the arms 199, 201 may have a thicker portion 247 to account for the thickness of the straps 112, 118, with the demarcation of a thinner portion 249 adjacent the greater thickness forming the hinges 213. The thinner portion 249 may be between the web portion 231 and the thicker portion 247, and offers improved flexibility.

FIGS. 2J-2M illustrate a variation of the connector in FIG. 2I. The connector 400 includes a buckle assembly 402 connected to a multi-directional strap mount 404. The strap mount 404 is integrally connected to the buckle assembly 402. The strap mount 404 is overmolded onto a rigid base part 408 of the buckle assembly 402, whereby the material of the strap mount 404 forming the overmold may be a thermoplastic elastomer (TPE) and the base part 408 is formed from a material more rigid than the TPE of the strap mount 404, such that the base part 408 does not bend when the strap mount 404 bends relative to the base part 408. The buckle assembly 402, as in the foregoing embodiments, has a lever 406, the base part 408, and a connecting part 410.

The multi-directional strap mount 404 extends in first and second directions DD1, DD2 at at least one oblique angle relative to a center axis B-B of the base part 408 to orient straps, as shown in other embodiments, according to the direction of the first and second mount parts 414, 416 from the mount body 412. The first and second directions DD1, DD2 may each be arranged at a different angle relative to the center axis B-B of the base part 408.

The first and second mount parts 414, 416 may be separated by a clearance 418 to enable the first and second mount parts 414, 416 to flex generally independently from one another and relative to the mount body 412. In this sense, the clearance 418 may not be uniform in width but rather may taper inwardly toward the mount body 412, and permits the first and second mount parts 414, 416 to pivot away or toward one another in rotational directions R1, R2 with the axis A being the inward point of the clearance 418 at the mount body 412.

Figure 2J:
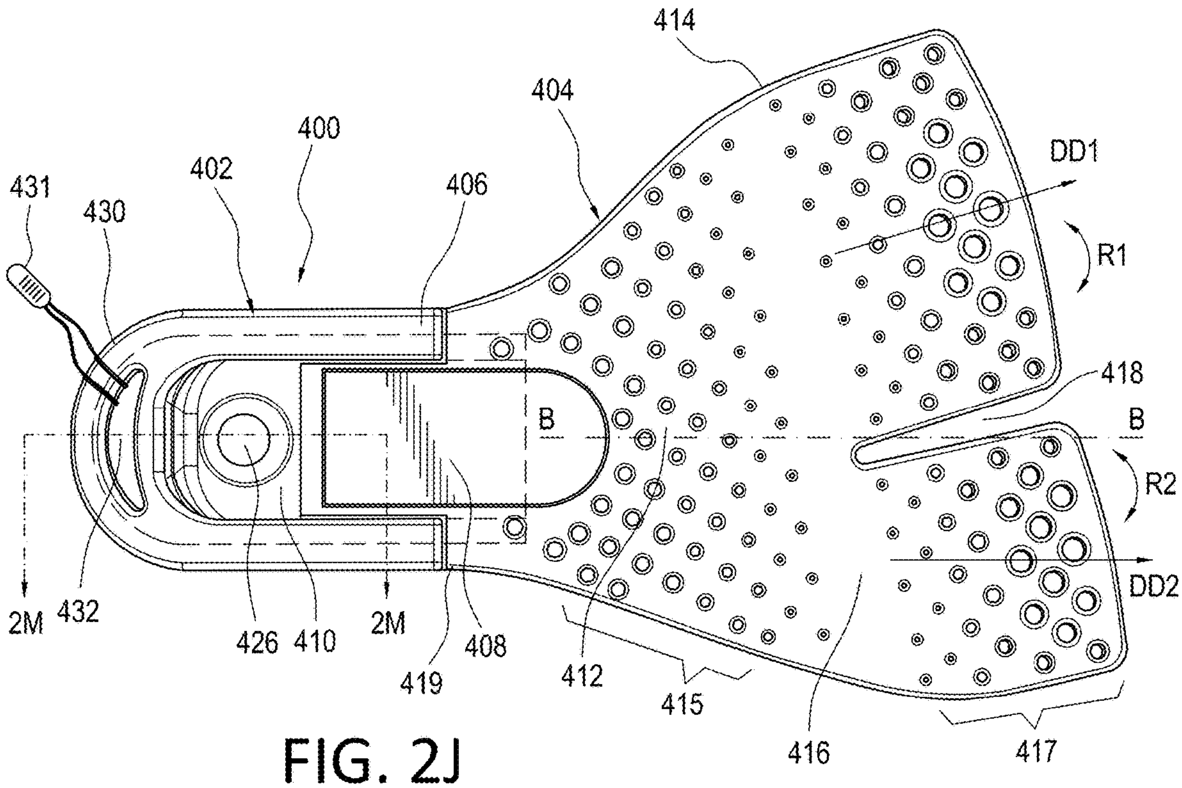
FIG. 2J is a top plan view of the connector of FIG. 2I.
Figure 2K:
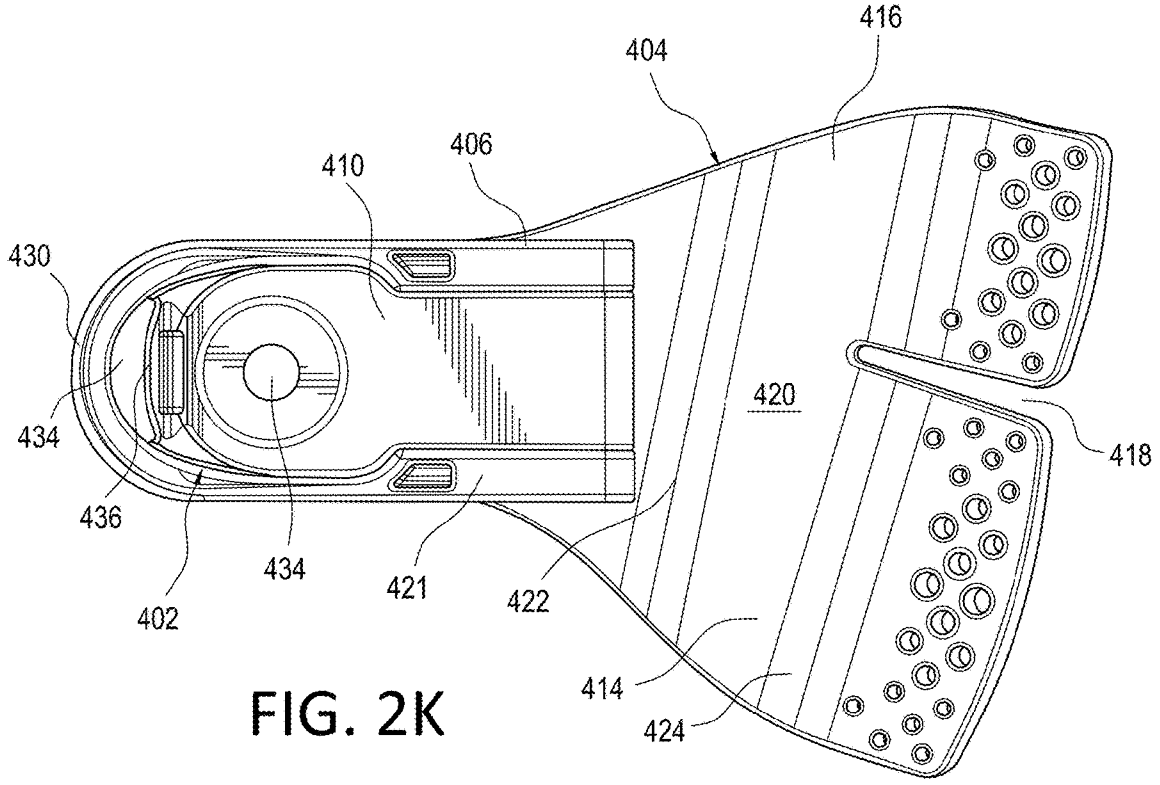
FIG. 2K is a bottom plan view of the connector of FIG. 2I.

As illustrated in FIGS. 2J and 2K, the first and second mount parts 414, 416 may be sized differently. The different sizing may be according to the type of straps that are secured to the mount parts, such that the first mount part 414 may receive or engage a dynamic force strap, as in FIGS. 1A and 1B, and the second mount part 416 may receive a circumferential strap. While the aforementioned embodiments illustrate the straps as being permanently secured (i.e., not having an adjustable connection to the strap mounts), the strap mounts may be configured with slots or otherwise be formed as a conventional D-ring to receive and have a strap adjustably secured thereto. In such a variation, the end portions of the mount parts 414, 416 may be provided with an elongate slot through which the strap may be looped, with the strap having means for securing to itself for adjustable or permanent (i.e., stitching or using a fastener) connection to the mount parts 414, 416.

The mount body 412, which is generally pliant and resilient, defines a recess 420 on an underside thereof (i.e. the side facing toward a user's body) to facilitate bending of the mount body 412 and first and second mount parts 414, 416 over the orthopedic device 100 or another device or the user's body about which the mount body 412 and first and second mount parts 414, 416 contour. The recess 420 results in a region of reduced thickness. The recess 420 may define graduated tapered sections 422 adjacent the base part 408, and graduated sections 424 adjacent or into the first and second strap mounts 414, 416. While the material forming the first and second mount parts 414, 416 is preferably pliant, the recess 420 and first and second tapered sections 422, 424 encourage bending of mount body 412 and the first and second mount parts 414, 416 in a direction about which the multi-direction strap mount 404 is biased (i.e., over the device or user's body, resulting in a reduced profile). The first and second graduated tapered sections 422, 424 may have different tapers or degree of tapering according to their location and the extent of bending that is desired of the mount body 412.

As shown in FIGS. 2J and 2K, the strap mount 404 generally flares away from the base part 408, and defines a greater width (as opposed to thickness) as it extends away from the base part 408.

The second tapered section 424 may result in thicker regions than in the first tapered section 422 since the mount parts 414, 416 may require a thicker profile to accommodate portions of the straps, particularly when the mount parts 414, 416 are molded over end portions of straps. When the first and second mount parts 414, 416 are molded onto and over end portions of the straps, the material of the mount parts cures and/or shrinks over the end portions of the straps to fixably secure to the material of the straps. As the first and second mount parts 414, 416 may be formed from a TPE, the straps may be formed from a textile that the TPE interlocks with as it cures so the first and second mount parts 414, 416 are integrally secured to the straps. In this sense, one cannot readily remove end portions of the straps from the first and second mount parts 414, 416 without cutting, tearing or by other means. The end portions of the straps are fixed in place in the first and second mount parts 414, 416, and cannot be adjusted at such location. This has the advantage of fixably securing the end portions of the straps to the connector, and permitting the strap to be adjusted elsewhere, if desired.

FIG. 2J illustrates how the mount body 412 defines a first set of perforations 415 proximate to the base part 408. The first set of perforations 415 are greater (i.e. larger and denser) near the interface of the mount body 412 to the base part 408 in part to provide flexure of the mount body 412 proximate to the base part 408. As the base part 408 is preferably formed from a rigid material, and is more rigid than the mount body 412 because the base part 408 generally retains or fully retains its shape as the mount body 412 flexes relative thereto, the first set of perforations 415 structurally increases the flexibility of the mount body 412. The first set of perforations 415 may only extend from one side of the mount body 412, as shown in FIGS. 2J and 2L, or extend fully through the mount body.

The mount body 412 also defines a second set of perforations 417 at the end portions of the first and second mount parts 414, 416, wherein the perforations increase (i.e. increase in size and density) toward the end of the first and second mount parts 414, 416. The number, shape and size of the perforations may vary according to the individual first and second mount parts 414, 416 through which they are located. The second set of perforations 417 are shown as extending fully through the first and second mount parts 414, 416, but can extend from only one side as in the first set of perforations 415.

The connecting part 410 may include a protrusion 426 or other traction element(s) (as depicted in FIG. 2B) to aid in pressing or releasing the buckle assembly 402. The first end 430 of the lever 406 defines an opening 432 through which a cable or other leverage element 431 may be secured to add more leverage to the lever 406 when bringing the connector 400 into an open configuration, as the leverage element 341 allows a user to grasp the leverage element 431 and apply less force to the connector 400, because the leverage element 431 has an advantaged location relative to the locking portions of the buckle assembly 402 compared to the first end 430. The lever 406 may include a grip feature 438, for example a more frictional and grippable overmolded material placed along the first end 430 of the lever 406. The traction element(s) 426, the leverage element 431, and grip feature 438 are offered to assist users with poor dexterity adjust the buckle assembly 402.

Figure 2L:
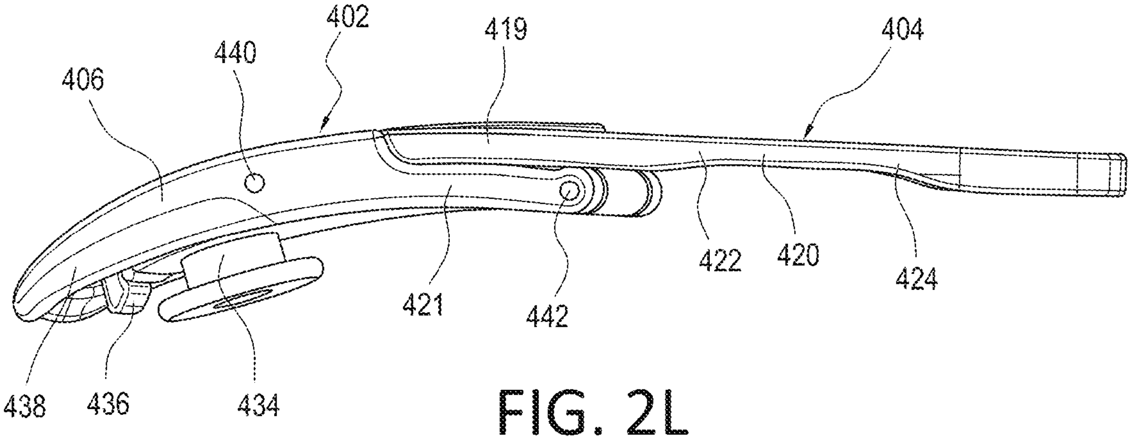
FIG. 2L is an elevational view of the connector of FIG. 2I.
Figure 2M:
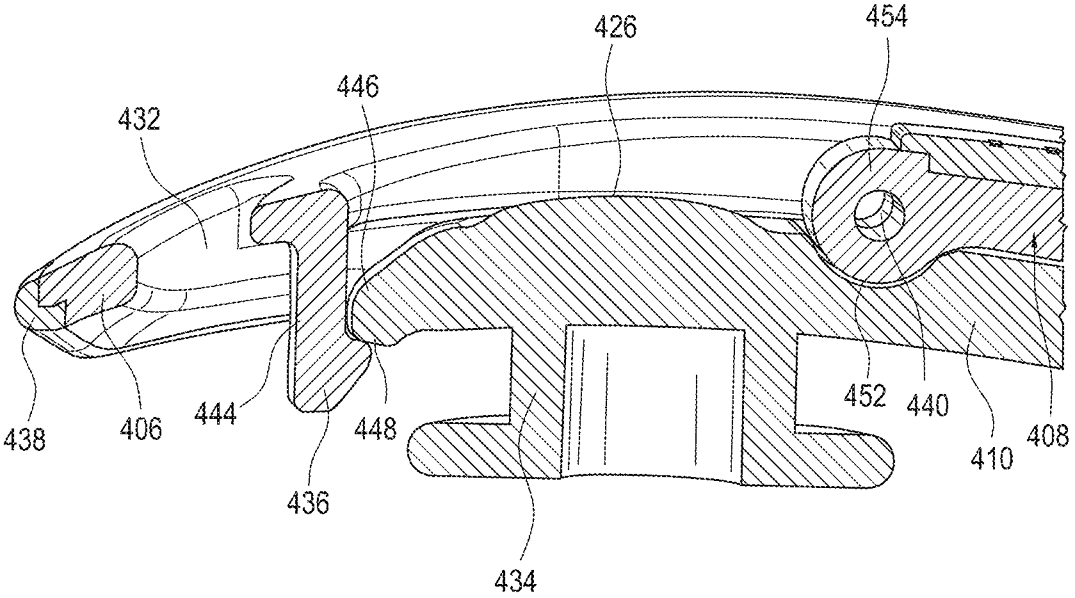
FIG. 2M is a sectional view taken along line 2M-2M in FIG. 2I.

FIGS. 2K-2M depict the connecting part 410 as having a locking part 434, with the connecting part 410 pivotally secured to the lever 406 at pivot point 442 with a pin. The lever 406 is secured to the base part 408 at pivot point 440. FIGS. 2J-2L illustrate how end portions 419 of the mount body 412 extend over shoulders or end portions 421 of the lever 406. The end portions 421 of the lever 406 are more rigid than the mount body 412, and the mount body 412 can bend over the end portions 421, to better bias about the buckle assembly 402 and thereby adhere to the orthopedic device 100 and the user's body. The strap mount 404 flares away from the buckle assembly 402 by having a width greater than the buckle assembly 402.

FIG. 2M shows the lever 406 as having an extension 444 carrying a tab 436 that is engageable with a lip 448 about a rounded portion 446 of the connecting part 410. This lip 448 and the tab 436 have geometries that allow the tab 436 to slide over the rounded end portion 446 with the extension 444 deflecting so that when the lever 406 is pressed fully towards a closed configuration, the lever 406, and particularly the extension 444 and tab 436 of the lever 406, ares guided over the rounded portion 446 enabling the lever 406 to be pressed at any place to secure with the connecting part 410, and therefore close the buckle assembly 402. The connecting part 410 has a recess 452 that may be rounded or arcuate into which a first end 454 of the base part 408 fits into when the lever 406 is snapped or secured to the connecting part 410, as discussed above.

Figure 2N:
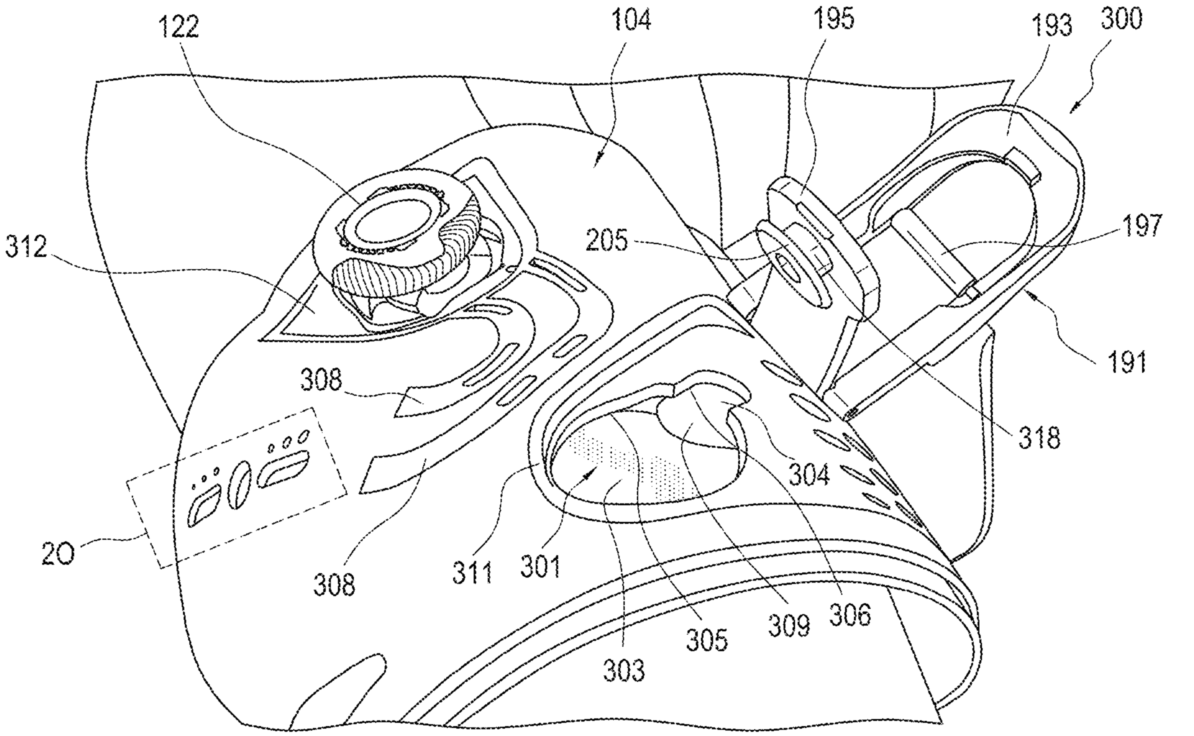
FIG. 2N is a perspective view showing a variation of a second shell from the embodiment of FIG. 1A with the connector of FIG. 2I.

FIG. 2N exemplifies a connection system 300 having the connector 191 arranged for simplifying and improving connection of the straps (shown in FIGS. 1A and 1B). The connection system 300 relies on a keyhole 301 having a first opening 303 leading into a second opening 304, wherein the first opening 303 is larger than the second, smaller opening 304. The locking part 205 of the connector 191 is arranged to be received by the first opening 303, and an extension 318 from which the locking part 205 extends can be moved and locked against the second shell 104.

A wall thickness 305 about the first opening 303 may be substantially thinner than a wall thickness 306 about the second opening 306, which is thicker than the wall thickness 305 to more stably hold the extension 318 firmly against the shell 104. The wall thickness 305 is relatively thinner about the first opening 303 to facilitate insertion of the locking part 205 within the first opening 303, and facilitate slipping the locking part 205 under an interior surface of the shell 104 within the second opening 304 and engaging the extension 318 against the periphery of the second opening 304.

The shell 104 defines different thicknesses to accommodate different features. The tensioning mechanism 122 is in an area of the shell 104 having a thicker or reinforced portion in part to stabilize the shell 104 and prevent inadvertent tampering of the tensioning mechanism 122 especially as greater degrees of tension are applied to the orthopedic device 100. The shell 104 defines a clearance or opening 312 to provide a user with access to the tensioning mechanism 122. The shell 104 may likewise have channels 308 for accommodating the cable extending from the tensioning mechanism 122. The shell 104 defines a recessed portion 311 about the connection system 300 to conceal at least in part the connector 191 and facilitate connection thereof to the shell 104.

A compressible element 309 may protrude into or underneath the second opening 304, and may be on a liner disposed along the interior surface of the shell 104. The compressible element 309 can bias the locking part 205 against the interior surface of the shell 104, either when the orthopedic device is worn or not worn. The compressible element 309 may be a foam or otherwise compressible material or set-up.

To aid in donning the locking part 205 and assure the correct strap is secured against the shell 104, the compressible element 309 is preferably color-coded or matches a color disposed on the locking part 205. The compressible element may be replaced by a colored area on the liner that matches the locking part 205.

Figure 2O:
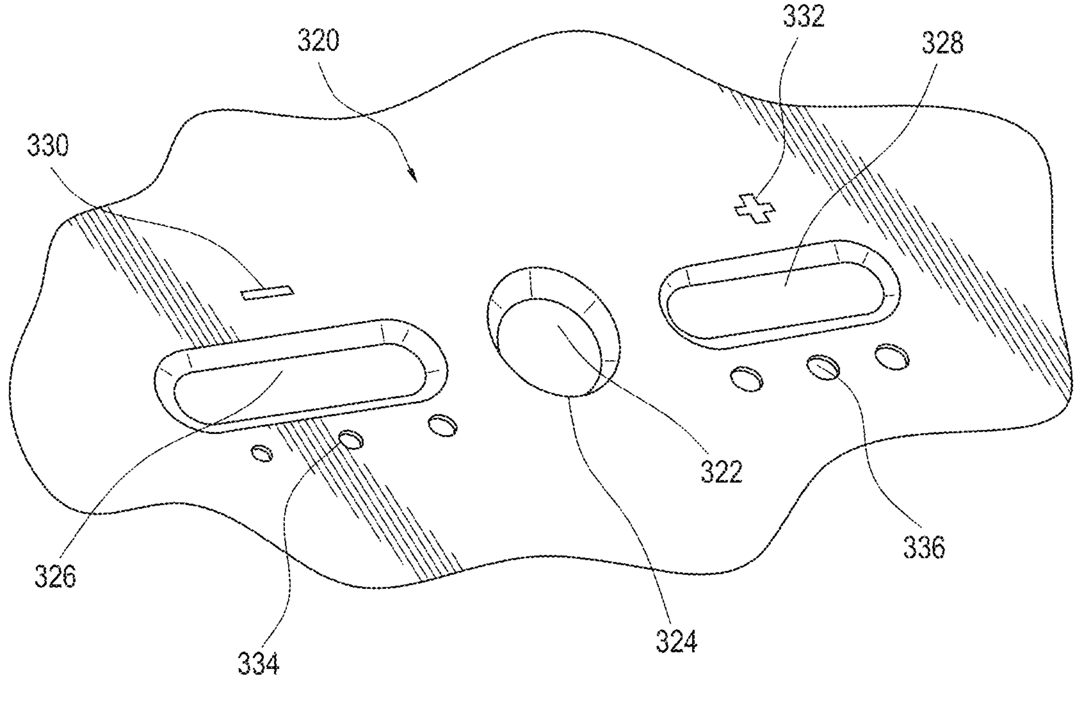
FIG. 2O is a detail view 2O of the dosing scale in FIG. 2N.

Referring to FIG. 2O, a dosing scale 320, as in the indicia 132 in FIGS. 1A and 1B, provides a relative indication of tension in the straps 112, 118. The dosing scale 320 provides a neutral opening 324 defined by the corresponding region of shell 104 whereat an indicator 322 is located when the strap has a neutral tension. The shell 104 defines first and second slots 326, 328 on opposed sides of the neutral opening 324, and includes corresponding indicia 334, 336 for each of the first and second slots 326, 328, whereby the further away the indicator 322 goes from neutral reflects decreased 330 or increased 332 degrees or amounts of tension. Advantageously, a user or clinician can have a relative understanding of tension in the strap by way of indicia 322, 334, 336 and the slots 326, 328, for both a decrease and an increase in tension. This arrangement mitigates a necessity to wind or unwind during donning and doffing by keeping the set tension in neutral.

The embodiments of the shell have improved contours with smaller and sleeker sizes, and are adapted to avoid pressure points. The shells provide flexible peripheral edges formed by flexible material applied in functional areas to create an integrated look and feel, and reduce a need for padding such that reduced profile flush padding can be used. All of these features advantageously provide that the device may have reduced cost and complexity, and may be less bulky and easier and more comfortable to use.

Figure 3:
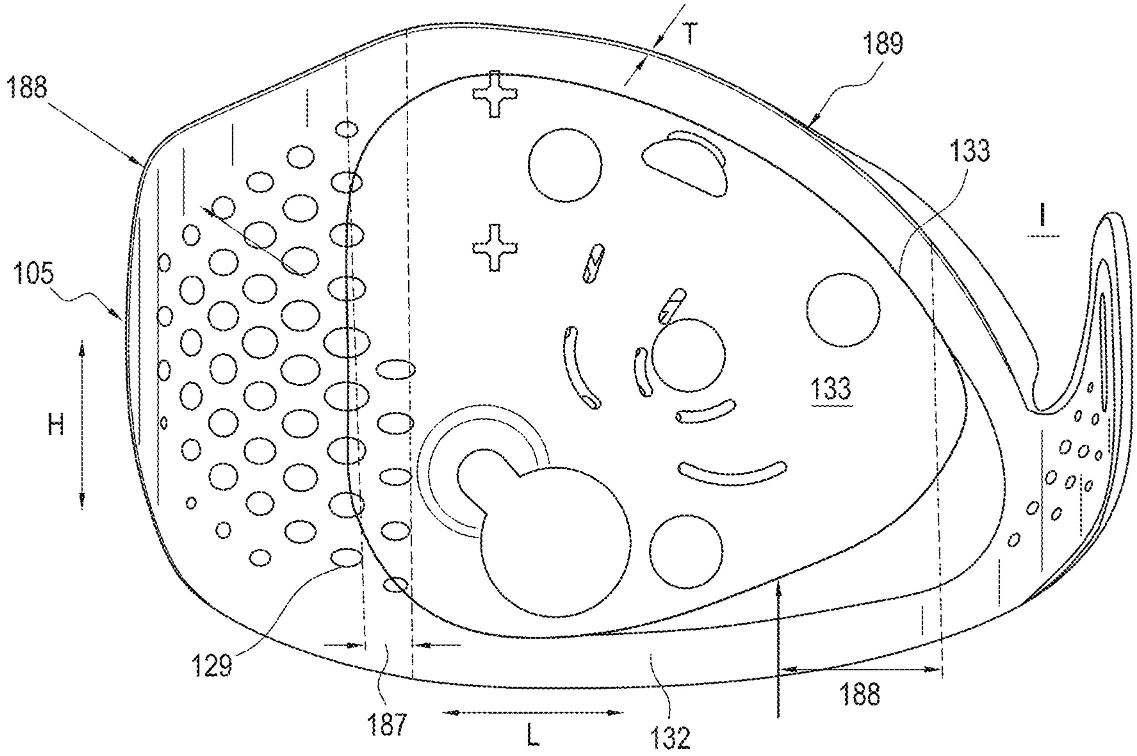
FIG. 3 is a schematic view of a variation of a shell in the orthopedic device of FIGS. 1A and 1B.

Referring to FIG. 3, another embodiment of an orthopedic device according to the disclosure is described, with particular attention given to shell 105. Shell 105 has a shell body 129 defining a varying thickness (T) along a length (L) of the shell 105, and defines at least one zone 187, 188 having a thinner thickness than in areas outside of the at least one zone 187, 188. The shell body 129 may have a varying thickness (T) according to a height (H) of the shell body 129, such that a thickness at a first height or portion of a height of the shell body 129 along the length (L) of the shell body 129 differs from a second height or portion of the height at the same location along the length (L).

The peripheral edge 132 has a first width 188 at a first location, and a second width 189 at a second location. The first width 188 is preferably greater than the second width 189. The peripheral edge 132 has an increased profile 133 arranged to extend about a user's tibia to provide additional flexure and padding of the shell 105 about the user's tibia. The peripheral edge 132 preferably extends more over one side surface 135 of the shell body 129 than another side surface of the shell body 129, for example, inner and outer surfaces of the shell body 129. The peripheral edge 132 may have variable relative extension about the side surfaces of the shell body 129.

Figure 4A:
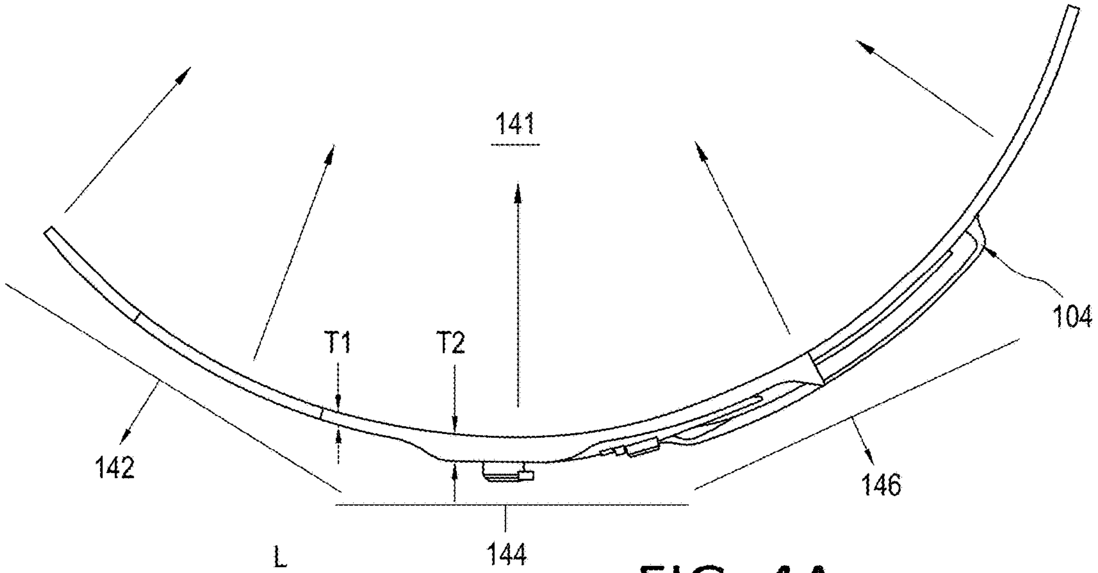
FIG. 4A is a top view showing zones of a shell in the orthopedic device of FIGS. 1A and 1B.
Figure 4B:
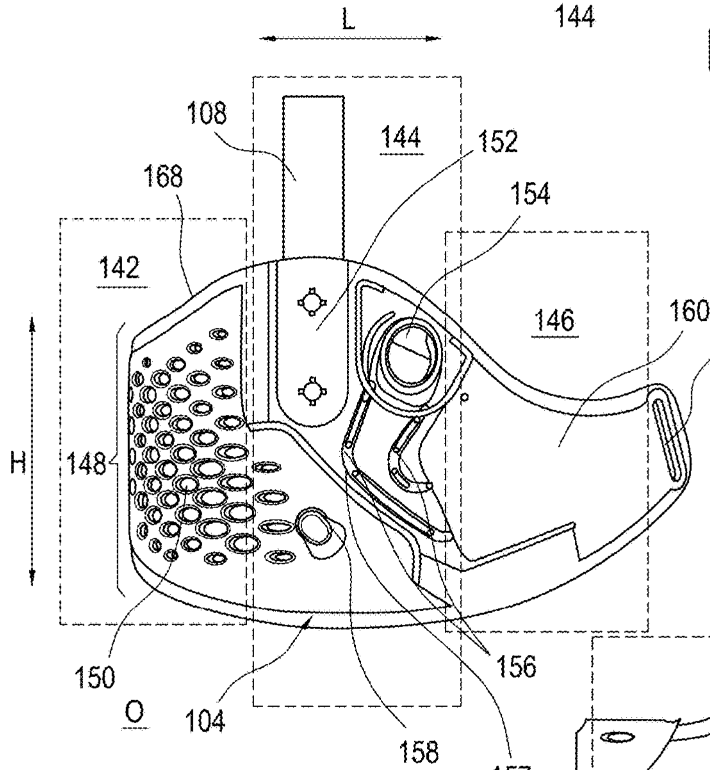
FIG. 4B is an elevational view of an outer side of the shell without an overlay in FIG. 4A.
Figure 4C:
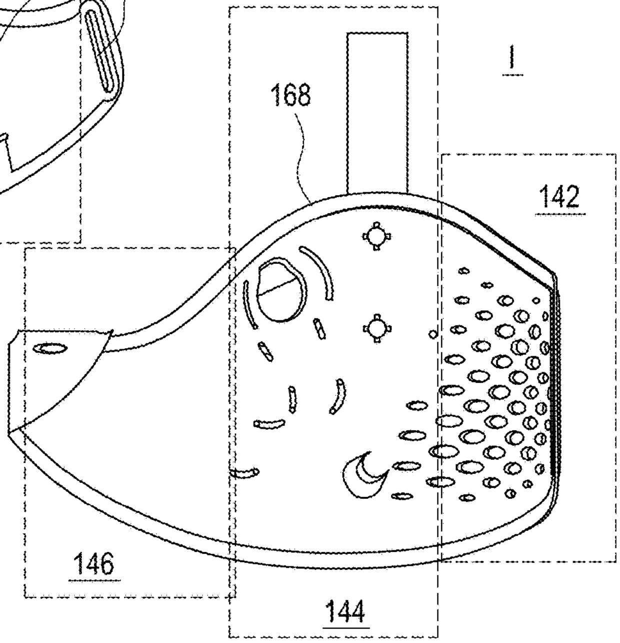
FIG. 4C is an elevational view of an inner side of the shell without an overlay in FIG. 4A.

Turning to FIGS. 4A-4C, the shell 102, 104 according to an embodiment of the present disclosure may be arranged to contour about a cavity draw direction 141 or about the user's leg, in at least three primary planes 142, 144, 146 along the length (L) of the shell 102, 104. The first primary plane 142 is preferably arranged generally posteriorly of the anterior-posterior plane, and/or of the first or second struts 106, 108, and defines a perforation region 148 including at least one perforation 150.

The second primary plane 144 defines a slot 152 for receiving the strut 106, 108, and a hook 138, 158 for receiving the buckle assembly 140 (not shown) adapted to secure onto the shell 102, 104 at the second primary plane 144. The second primary plane 144 defines a base 154 for receiving the tensioning mechanism 120, 122 movable relative to the shell 102, 104. The second primary plane 144 defines at least one guide 156 being at least partially enclosed by a closure 157.

A thickness (T1) of the first primary plane 142 is less than a thickness (T2) of the second primary plane 144. The thickness (T2) is variable along the length (L) according to the features defined by the shell 102, 104 within the second primary plane 144, for example the strut slot 152, the base 154 and the cable guides 156. The thickness (T2) likewise varies along the height (H) of the shell 102, 104 through the second primary plane 144 according to the features defined by the shell 102, 104. The second primary plane 144 is arranged generally along the anterior-posterior plane of the orthopedic device 100.

The third primary plane 146 defines a strap extension 160 defined generally elongate along the length (L) of the shell 102, 104. The strap extension 160 defines a strap slot 164 adapted to receive the circumferential strap 116, 118. The third primary plane 146 may be longer than the first primary plane 142. The third primary plane 146 generally extends anteriorly from the anterior-posterior plane of the orthopedic device 100 and is arranged to extend about the tibia of the user.

Referring to FIGS. 5A-5C, another embodiment of first and second shells 102, 104 defining shell bodies 128, 129, and overlays 130, 131 extending over the shell bodies 128, 129. The overlays 130, 131 define peripheral edges 132 about the shell bodies 128, 129 is depicted, and overlay areas defining various features of the first and second shells 102, 104. The peripheral edges 132 are preferably more flexible than the shell bodies 128, 129. The peripheral edges 132 are interlocked with a peripheral edge 137 (as shown in FIGS. 4B and 4C) of the shell bodies 128, 129.

The features defined by overlays 130, 131 may include strap receiving areas 161, 162, whereby portions of the overlays 130, 131 are contoured relative to the shell bodies 128, 129. The overlays 130, 131 are adapted to extend over features formed by the shell bodies 128, 129, and provide a generally continuous surface without interruption or hard edges, which increases comfort and minimizes bulk; however, the overlays 130, 131 may define ridges, troughs, and shapes as necessary to accommodate features.

The overlays 130, 131 can interlock components, such as the struts 106, 108, to the shell bodies 128, 129. The overlays 130, 131 may conform in shape to the contours of the strut 106, 108. The overlays 130, 131 can also form pockets 170, 171 for receiving the straps 112, 114.

As shown in FIG. 5A, the first shell 102 forms a perforated region or pattern 148 having a plurality of openings 150 arranged in patterns 174, 176, 178 to facilitate bending of the first shell 102 according to predetermined paths or directions X-X, Y-Y and Z-Z, respectively. The pattern 148 is proximate a strap slot 163 formed by a periphery 168 of the shell body 128 and generates a lighter and more flexible structure in desired locations. By providing greater flexure near the circumferential strap 116, the first shell 102 can contour the anatomy of the user more closely and comfortably by gently yielding to the anatomical contours while the first shell 102 maintains its integrity, thereby reducing bulk without sacrificing effective bracing.

The pattern 148 preferably defines a plurality of openings 150*a* that have a greater size generally in the middle of the pattern 148, with the openings 150*a* tapering in size toward ends of the pattern 148. The pattern 148 is arranged generally in a diagonal arrangement that anatomically follow contours by which the shell body 128 proximate the strap slot 163 bends on a user. The pattern 148 may comprise localized patterns 174, 176, 178 defined by multiple rows of such openings 150*a*, defined in part by the sequential difference in sizes of the openings 150*a*.

The localized patterns 174, 176, 178 are not simply defined by differently sized openings 150*a*, but may also be defined by the shape of the openings 150*a* such that the shape, in addition to size, facilitates contouring of the first shell 128. In the depicted example, the openings 150*a* have an oval shape that lead or facilitate bending in a particular direction but permitting less bending in other less-desired directions.

A first dimension (i.e., length) of the openings 150*a* has a length greater than a second dimension (i.e., width), and such first dimension (length) leads in the first direction whereby flexure is desired, and the second dimension (width) may be in a second direction whereby flexure should be inhibited or less desired. Likewise, the openings 150*a* may be along the direction X-X. Clusters of openings 150*a* may diminish in size and density, as shown by 150*b*, as the pattern dissipates.

The pattern 148 exemplifies how the directions Y-Y, Z-Z are not limited to a single direction. The directions Y-Y, Z-Z intersect whereby both have openings 150 that are greater in size and/or occurring in greater density at an area requiring more flexure, and conversely diminish to areas of the shell body 128 either requiring less flexure assistance, such as at the edges, or areas where flexure is less desirable, such as proximate the strut 106, 108. The overlay 130 may delimit the extent of the pattern 148.

Features formed by or extending from the shell 102 may be arranged according to the pattern 148. For example, hook 138 is arranged generally in the direction Z-Z so that as the first shell 102 bends according to the pattern 148, the hook 138, which may couple to a strap, is generally aligned with the flexure of the first shell 102. Hook 139 arranged on shell 104 may be similarly configured along with analogous patterns of apertures performing similar functions.

In areas of the first shell 102 not requiring overlay, islands 165, 166 may be formed where the overlay 130 does not extend over the shell body 128. The islands 165, 166 may be in areas where it is undesirable for the tensioning mechanism 120, 122 to rub against the overlay, particularly since it is preferable that the shell bodies 128, 129 have a hardness greater than the hardness of the overlay 130, 131.

Referring specifically to FIGS. 5B and 5C, another feature is the pocket 171 formed over the shell body 129. The overlay 131 defines a portion 183 forming a clearance 184 relative to a surface of the shell body 129 to accommodate the strap 114. The pocket 171 enables the strap 114 to be received without interference by either the shell body 129 and the overlay 131. It is preferable that the portion 183 extends or protrudes outwardly relative to the shell body 129. The clearance 184 is preferably minimal to maintain a streamlined profile to the orthopedic device 100; however, the height of the clearance 184 can be modified to protrude depending on the design specifications. The pocket 171 may form transition portions 181, 182 that blend into or taper in height relative to the shell body 129. The pocket 171 may be sized in length (generally perpendicular to the height) to allow for the strap 114 to articulate within the pocket 171. The first shell 102 may similarly have a pocket 171.

The pocket 171 or feature of the overlay 131 may blend into or connect to another feature 180 that may form a channel for accommodating a cable or elongate element of adjustment mechanism 122. The overlay 131 has a significant advantage in that it can be formed over the shell body 129 and not only just provide a flexible edge portion, but it can also be used to cover features on the shell bodies 128, 129, reducing bulk and risk of damage to the components.

Figure 5D:
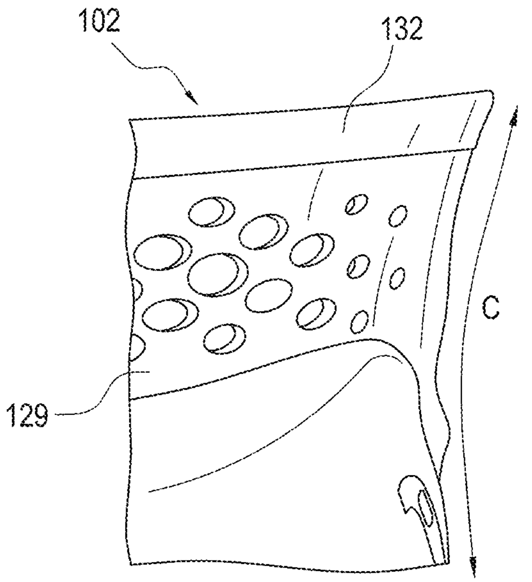
FIG. 5D is a detail view from FIG. 5A.

FIG. 5D illustrates how the first shell 102 may have a contour C, particularly when it is configured as a thigh shell 102. The contour C is defined as flaring outwardly generally at the proximal end of the shell 102 among both the shell body 129, and the peripheral edge 132. The contour C leads to better fit and comfort to the wearer, by more closely conforming to the shape of a thigh, particularly at the proximal end thereof.

Figure 6B:
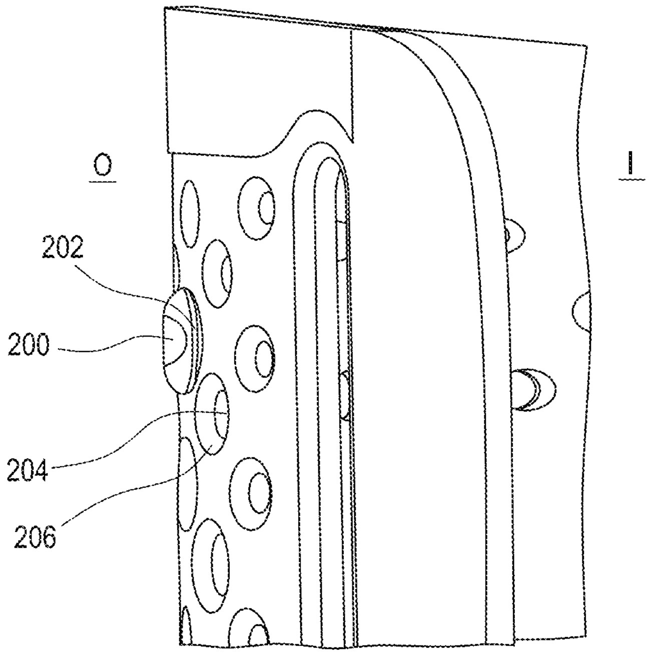
FIG. 6B is another schematic view of the insert attached to the shell in FIG. 6A.
Figure 6A:
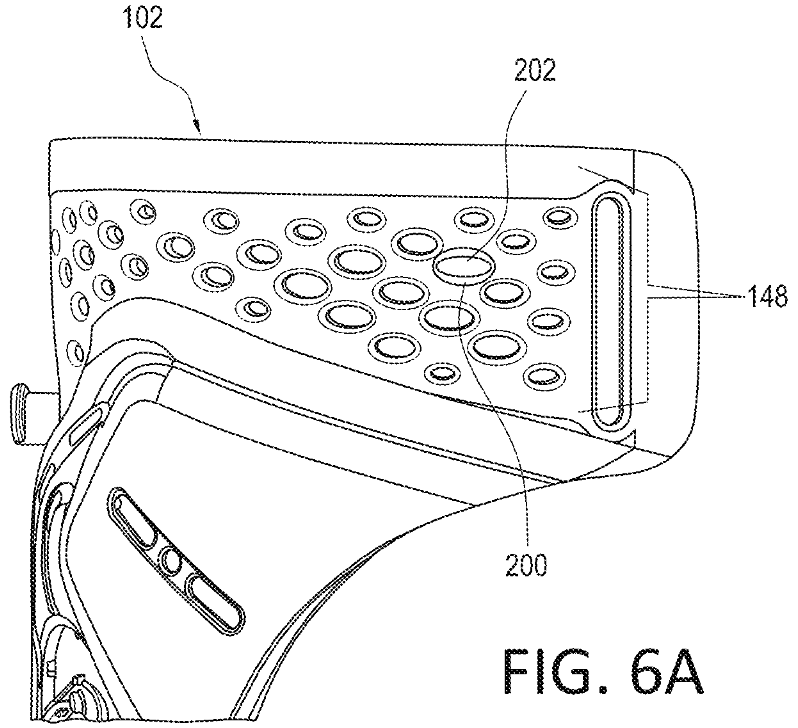
FIG. 6A is a schematic view showing an insert attached to a shell in the orthopedic device of FIGS. 1A and 1B for securing a liner to the shell.

FIGS. 6A and 6B exemplify means for eliminating hook-and-loop fastener systems when applying a liner to the orthopedic device 100. Specifically, the liners or padding are removably mounted to the shells in a manner that is quick and secure, without the necessity of aggressive hook-and-loop systems, which can be difficult to use, non-durable, and imprecise. Specifically, the liner 136 (not shown) includes an insert element 200 adapted to fasten to the shell 102, 104 by engaging about a preselected opening 202 defined by the shell 102. The insert element 200 can preferably only engage about and extend through the preselected opening 202 among the pattern of openings 148. In this manner, the insert element 200 is repeatedly secured to the same spot on the shell, to assure proper placement of the liner 136 against the shell 102, 104. Such an arrangement provides precision in locating the liner 136 not necessarily afforded by hook-and-loop fastener systems. Such an arrangement is also simpler and easier for users to execute.

The preselected opening 202 defines a through-hole 204 through which the insert element 200 extends from an inner side (I) of the shell 102, 104 to the outer side (O) of the shell 102, 104. A recess 206 surrounds an outer side (O) of the through-hole 204 into which the insert element 200 is received. While other openings may have a similar configuration, it is preferable that the preselected opening 202 is only sized and configured for receiving the insert element 200. There may be other preselected openings at other regions of the shell 102, 104, but it is preferable that only one opening 202 is provided in a particular or predetermined region to assure proper placement of the liner 136.

The shell 102, 104 is substantially rigid compared to the insert element 200 adapted to flexibly extend into or squeeze through the preselected opening 202. The insert element 200 preferably extends over the outer surface (O) of the shell 102, but does so in a manner that avoids the insert element 200 from being unintentionally dislodged from the preselected opening 202 and from extending too much from the shell 102, 104, thereby maintaining a sleek profile.

FIGS. 7A-7F exemplify means for providing frame extensions to accommodate users with a high body mass index or higher-than-normal amounts of soft tissue that need a shell of a larger area, and to better protect the thigh and dynamic force straps as they depart from the shell. While the aforementioned embodiments are focused on smaller and more streamlined frame components, such as the shells, while still preserving necessary strength and integrity, some users have larger anatomy and may benefit from larger shells to accommodate their anatomy. Rather than provide different sized shells, thus adding to cost and inventory, the improved shells described above may be retrofitted with frame extensions that can be added to the existing orthopedic device to serve those users with larger anatomy.

A purpose for the frame extension is to increase the size of the shell with an over-molded liner, in this case the frame extensions 210, 294 described below. The frame extensions 210, 294 may have a gradual decrease in stiffness closer to the edge of frame extensions 210, 294 to reduce pressure points and increase comfort. The frame extensions 210, 294 extends under the strapping system to create a larger surface area to reduce pressure points or a cutting effect from straps or edges that users may complain about and which may interfere with user compliance.

Specifically, a frame extension 210 is provided to extend along a periphery 218 of the standard-sized first shell 102. The frame extension 210 extends adjacently along an entirety of the periphery 218 of the first shell 102. The frame extension 210 defines an upper extension 212 adjacent the periphery 218 of the first shell 102, and a portion of the upper extension 212 extends underneath a segment of the first circumferential strap 116. The upper extension 212 extends a substantially greater length from the periphery 218 of the first shell 102 proximate and under the circumferential strap 116, than it does from areas of the frame extension 210 adjacent the upper extension 212. The areas preferably have a generally uniform width extending adjacently from the periphery 218 of the shell 102. The upper extension 212 generally extends perpendicularly relative to the first strut 106.

The frame extension 210 defines a strap extension 214 extending from the frame extension 210 along and under a segment of the first dynamic force strap 112, the strap extension 214 having a strap slot 215 through which the first dynamic force strap 112 extends. The strap extension 214 extends generally obliquely anteriorly relative to the first strut 106.

The frame extension 210 defines a lower extension 216 extending obliquely posteriorly relative to the first strut 106 such that the second dynamic force strap 114 extends over the lower extension 216. The lower extension 216 flexibly extends from the area due to a living hinge 221.

The frame extension 210 may be substantially rigid or flexible. The liner may extend across the shells and the frame extension 210, thereby unifying the corresponding shell 102 and the frame extension 210. The frame extension 210 may define thinned regions that lie underneath the shell 102 and fasten thereto.

Figure 7A:
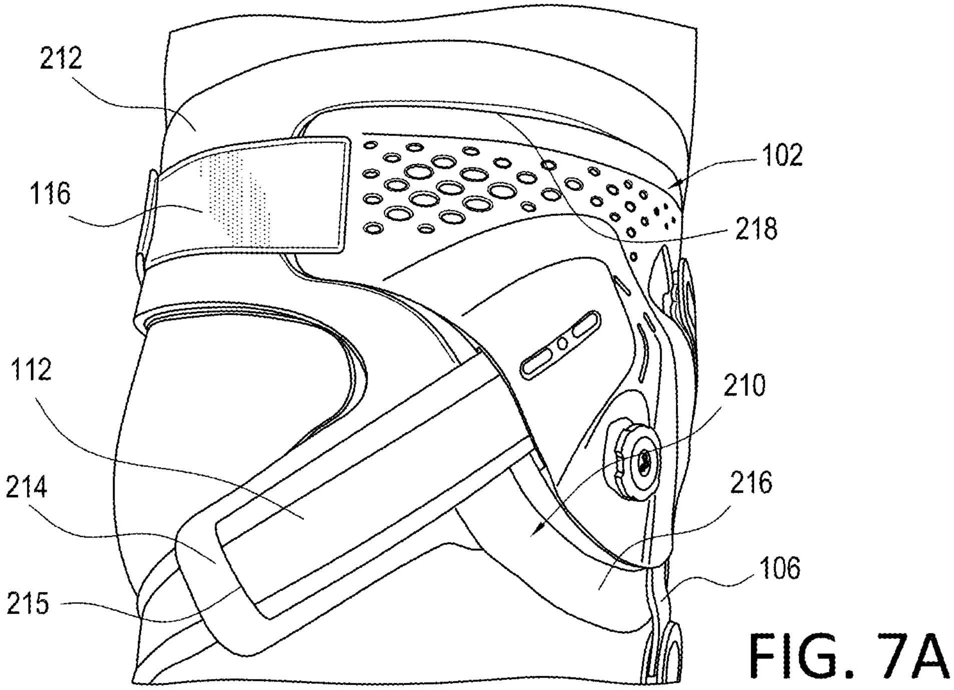
FIG. 7A is a first schematic view of a peripheral shell extension.
Figure 7B:
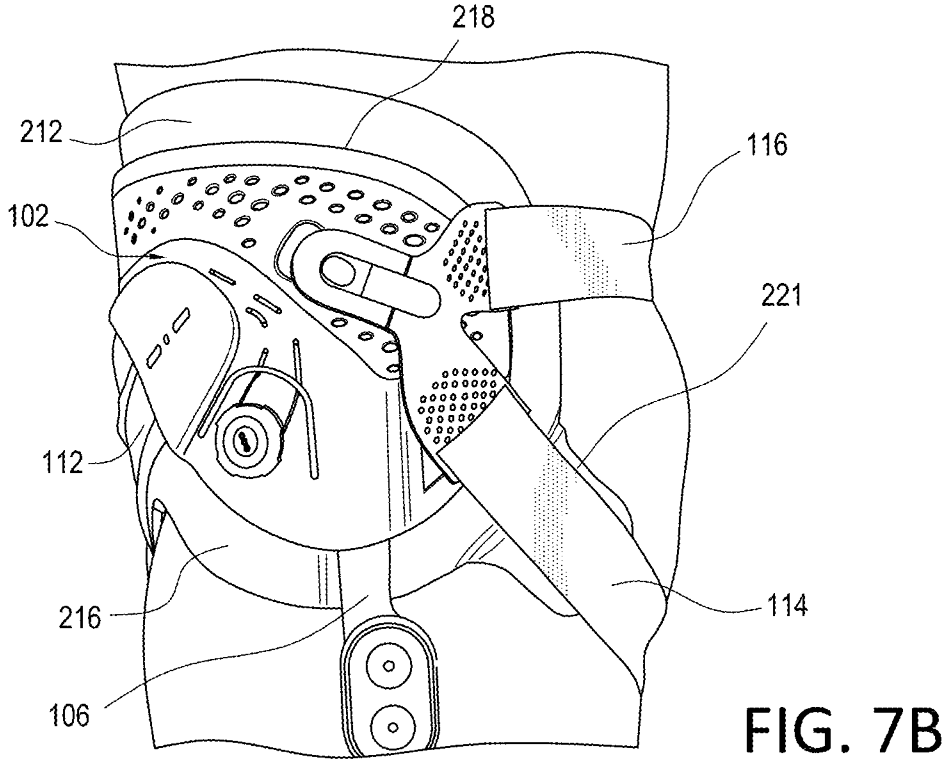
FIG. 7B is a second schematic view of the peripheral shell extension of FIG. 7A.
Figure 7C:
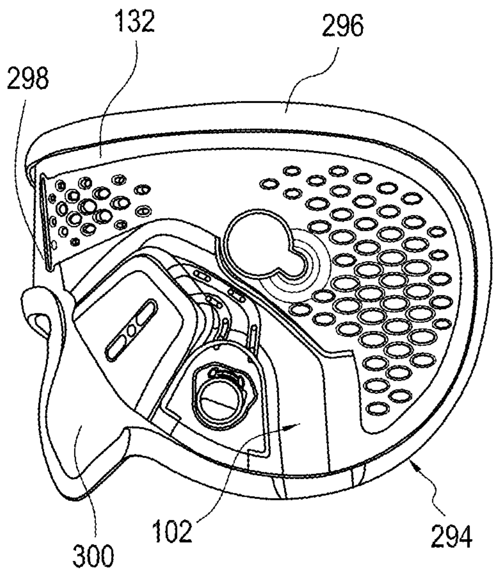
FIG. 7C is a schematic perspective view of another embodiment of a peripheral shell extension.
Figure 7D:
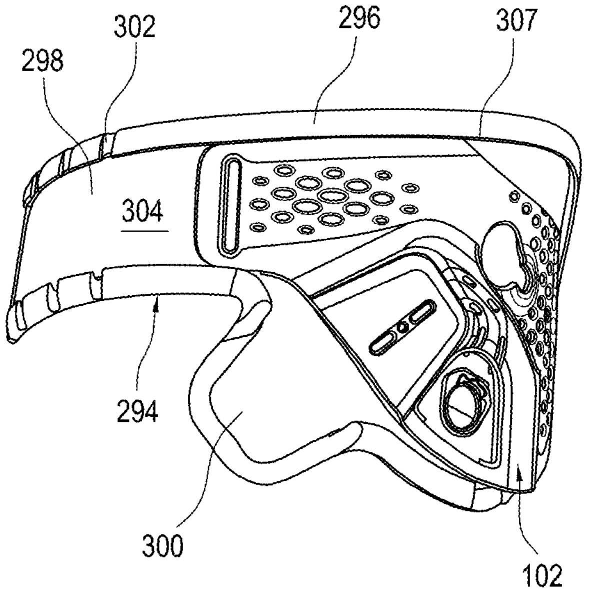
FIG. 7D is another schematic perspective view of the peripheral shell extension of FIG. 7C.
Figure 7E:
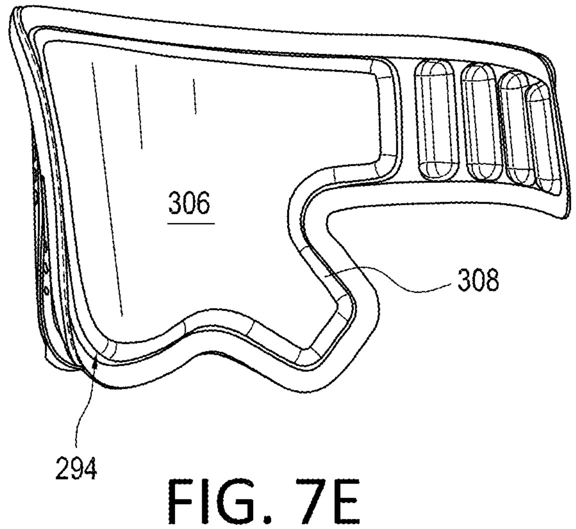
FIG. 7E is a schematic perspective view of a rear surface of the peripheral shell extension of FIG. 7C.
Figure 7F:
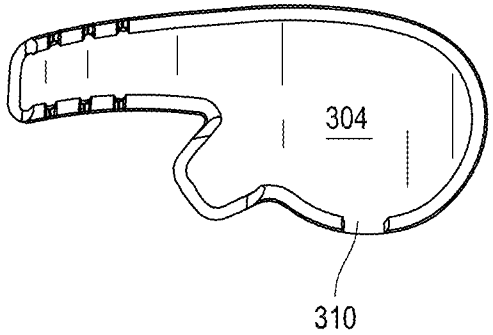
FIG. 7F is a plan view of a front surface of the peripheral shell extension of FIG. 7C.

FIGS. 7C-7F exemplify a flexible frame extension 294 formed integrally as a liner and frame extension of the aforementioned shell 102 in FIGS. 7A and 7B. The frame extension 294 has an outer surface 304 that lies along the shell 102, but has an upper extension 298 and a strap extension 300, that both extend beyond the periphery of the shell 102 and in the path of the circumferential strap and dynamic force strap. The frame extension 294 may be secured to the shell 102 according to the manner described in connection with FIGS. 6A and 6B.

To augment the soft overmolded peripheral edge 132 in the aforementioned embodiments, the frame extension 294 further defines a supplementary peripheral edge 296 that extends beyond the peripheral edge 132 of the shell 102. The supplementary peripheral edge 296 receives the peripheral edge 132 along an inner edge or lip 307 so the supplementary peripheral edge 296 and the peripheral edge 132 are snugly engaged or in contact with one another. The inner edge or lip 307 preferably extends over the peripheral edge 132 of the shell 102 for a smooth transition between the shell 102 and the frame extension 294. The inner edge or lip 307 preferably extends over the substantially or all of the perimeter of the shell 102.

The frame extension 294 has an outer surface 304 along which the shell 102 lies, and the frame extension 294, while being more flexible than the shell 102 to adapt to the contours of the user's anatomy, has sufficient rigidity (more rigid than the straps) to better stabilize the orthopedic device 100 on the user. Because the exact size of a particular user may be unknown, and to better accommodate many users with a single frame extension profile, the frame extension 294 is adapted to be trimmed in length along the upper extension 298. Breaks 302 in the supplementary peripheral edge 296 are provided as trim lines to permit trimming of the length of the upper extension 294. An additional break(s) 310 may be provided to correspond to features of the orthopedic device, such as the struts, so the overall profile is not substantially altered despite the addition of the frame extension 294.

An inner surface 306 likewise may serve as padding for the shell 102, and a border 308 is located inwardly from the supplementary peripheral edge 296 and generally corresponds to the peripheral edge 132. The border 308 may provide a comfortable, pressure-relieving profile that minimizes and evenly distributes pressure against a user's skin, especially near edges of the shell 102 where tension from the straps may be felt most acutely.

Figure 7G:
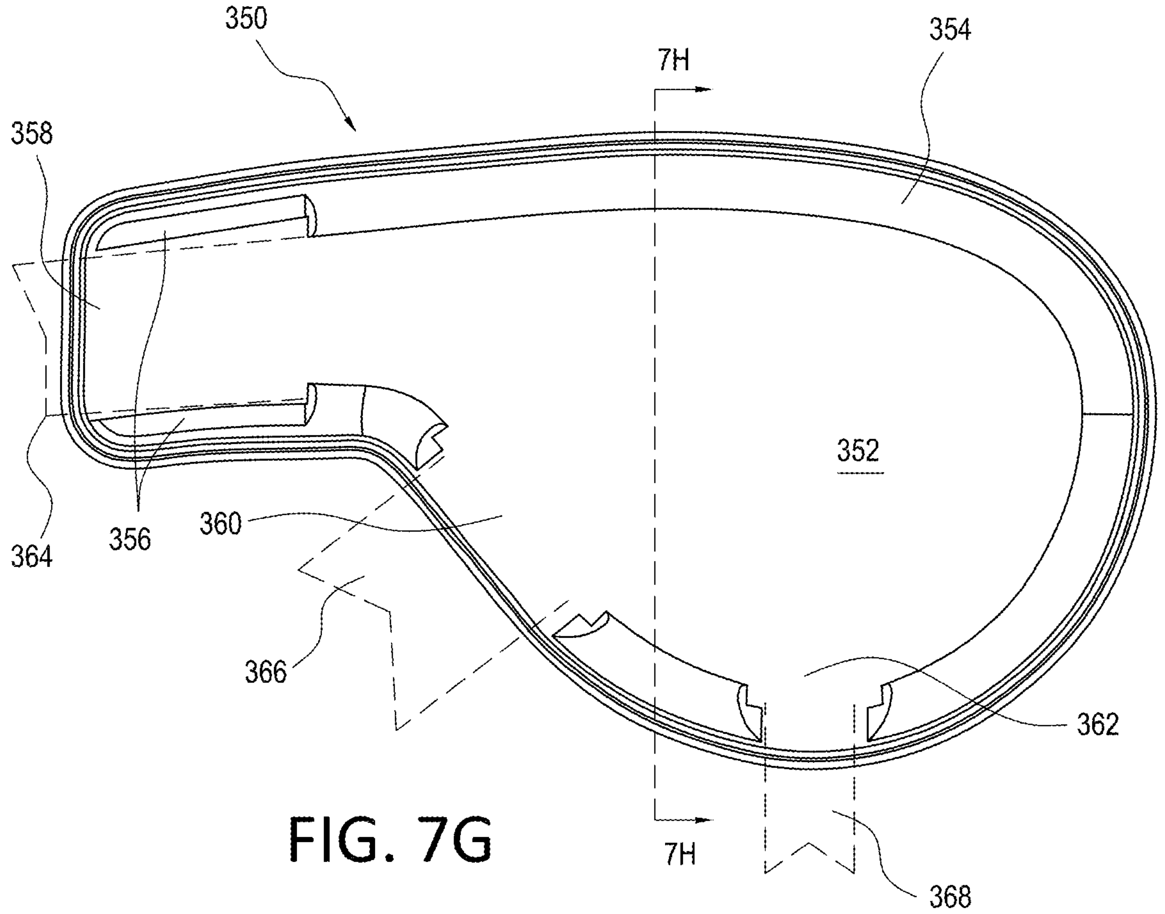
FIG. 7G is a plan view of another embodiment of a peripheral shell extension.
Figure 7H:
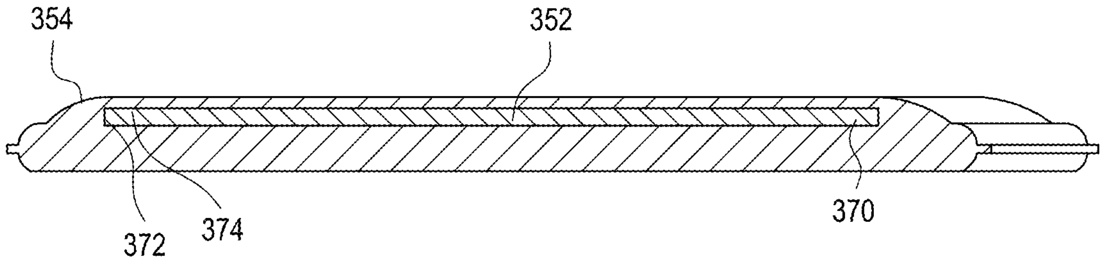
FIG. 7H is a cross-section of the peripheral shell extension taken along line 7H-7H in FIG. 7G.

FIGS. 7G and 7H depict another embodiment of a frame extension 350. The frame extension 350 defines an outer surface 352 having a peripheral edge 354 adapted to grab a shell 102, 104, as in the embodiment of FIGS. 7C-7F. The peripheral edge 354 has discrete portions about the periphery of the outer surface 352, with gaps or clearances 358, 360, 362 for accommodating straps and other features of the orthopedic device 100, such as straps 364, 366, and strut 368. The frame extension 350 may likewise have peripheral features 356 that transition to provide reinforcement about the edge of the frame extension 350, or whereat the shell 102, 104 terminates.

FIG. 7H depicts a cross-section of FIG. 7G, and shows how the peripheral edge 354 has an overlapping configuration 370 with a height 372 and a ledge 374 that overhang the shell (not shown). The peripheral edge 354 may be flexible to snugly secure to the shell 102, 104.

Figure 8A:
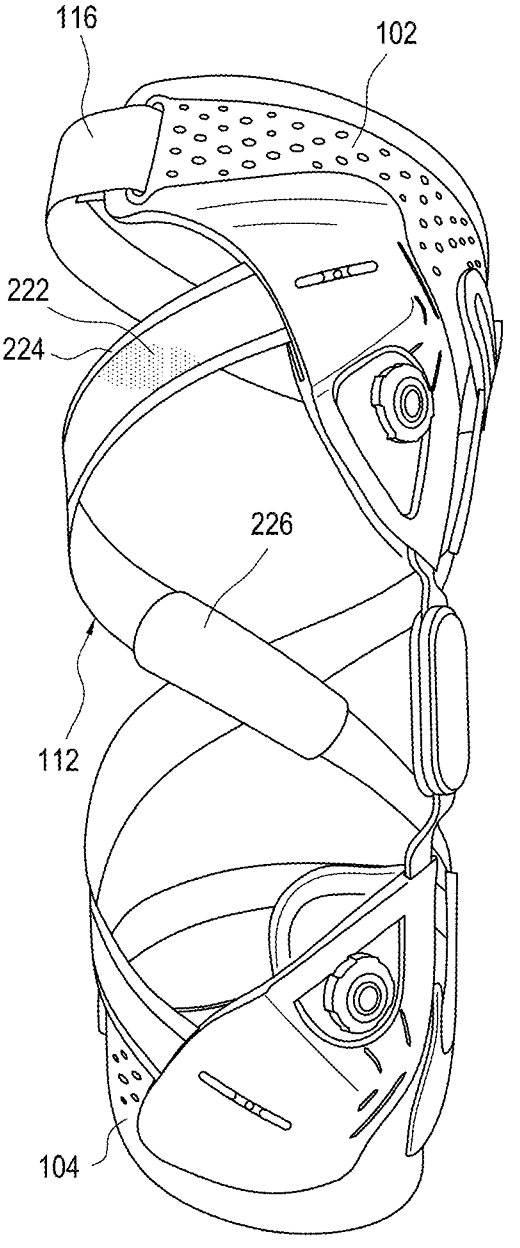
FIG. 8A is a perspective view of a variation of a strap assembly in the orthopedic device of FIG. 1A.
Figure 8B:
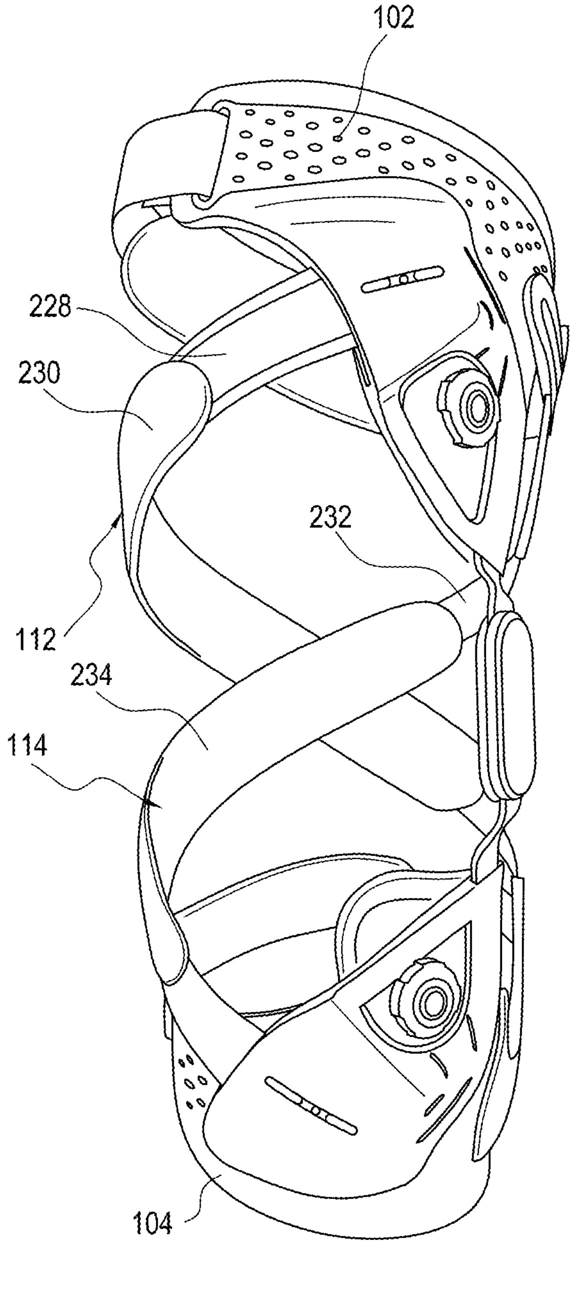
FIG. 8B is a perspective view of another variation of a strap assembly in the orthopedic device of FIG. 1A.
Figure 9A:
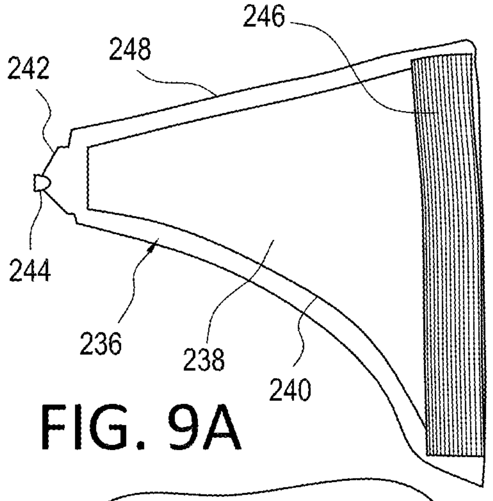
FIG. 9A is a plan view of a sleeve for an orthopedic device.
Figure 9B:
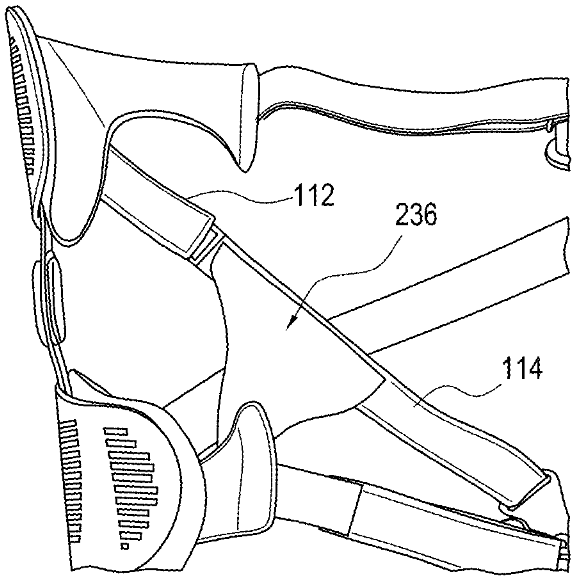
FIG. 9B is a perspective view showing the sleeve of FIG. 9A attached to a strap assembly.
Figure 9C:
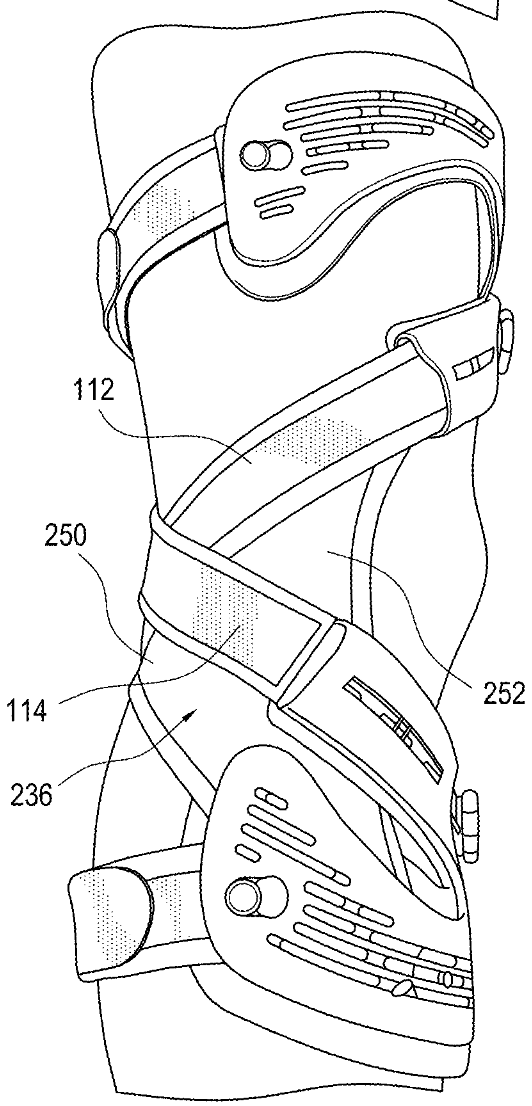
FIG. 9C is a perspective view of the sleeve of FIG. 9A in the orthopedic device of FIG. 1A.
Figure 9D:
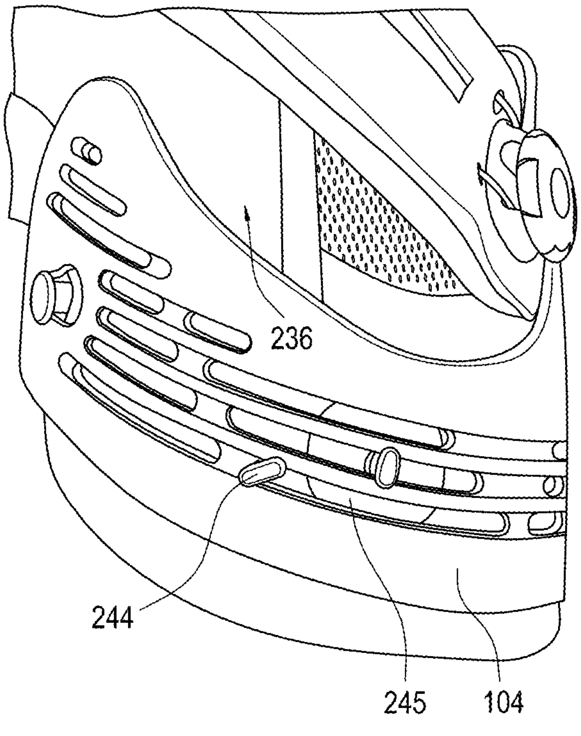
FIG. 9D is a perspective view showing how the sleeve of FIG. 9A is attached to the orthopedic device.

FIGS. 8A and 8B show configurations of the straps. FIG. 8A exemplifies the first dynamic force strap 112 as including an inelastic central portion 222 bordered by a pressure relieving portion 224 having padding properties greater than the inelastic central portion 222. The inelastic central portion 222 preferably overlies the pressure relieving portion 224. The pressure relieving portion 224 may surround the inelastic central portion 222, or the inelastic central portion 222 may overlie the pressure relieving portion 224, either along inner and outer sides of the pressure relieving portion 224. The first dynamic force strap 112 further includes a pad 226 between the first and second shells 102, 104.

FIG. 8B shows the first dynamic force strap 112 as defining a central portion 228 formed by an inelastic material, and a pressure relieving portion 230 surrounding the central portion 228 only between the first and second shells 102, 104. Both the first and second dynamic force straps 112, 114 have a central portion 228, 232 surrounded by a pressure relieving portion 230, 234 located only between the first and second shells 102, 104. The pressure relieving portions 230, 234 may comprise a soft overmold material, for example TPE. The pressure relieving portions 230, 234 avoid extending to the shells 102, 104, minimizing the bulk of the components of the orthopedic device 100.

FIGS. 9A-10C show sleeve embodiments selectively attachable to the orthopedic device 100. The addition of sleeve embodiments according to the disclosure may be desirable to some users to have added proprioception when wearing the orthopedic device 100, and to at least partially distribute pressure about the leg.

FIGS. 9A-9D show a sleeve 236 arranged to extend about only a portion (short of an entirety) of a circumference of the orthopedic device 100. The sleeve 236 has a segment 246 attachable directly to the first dynamic force strap 112, and defines a fastener arranged to engage the first dynamic force strap 112. The sleeve 236 has a main panel 238 defined by a stretchable and breathable material. The sleeve 236 has an edge binding 240 extending about the main panel 238 defined by a thicker material than the material forming the main panel 238.

The sleeve 236 has a triangular profile 248 arranged to extend along both the first and second dynamic force straps 112, 114 along a posterior side of the orthopedic device 100. The sleeve 236 defines a bracket 242 at an end portion of the sleeve 236, and a hook 244 extending outwardly from the bracket 242. The hook 244 is arranged to engage the second shell 104 about an opening 245 and tension the main panel 238 of the sleeve 236 between the first dynamic force strap 112 and the second shell 104, thereby defining a first section 250 between the second shell 104 and the second dynamic force strap 114, and a second section 252 between the first and second dynamic force straps 112, 114. The sleeve 236 extends along a side of the orthopedic device 100 opposite the hinge 110.

Figure 10A:
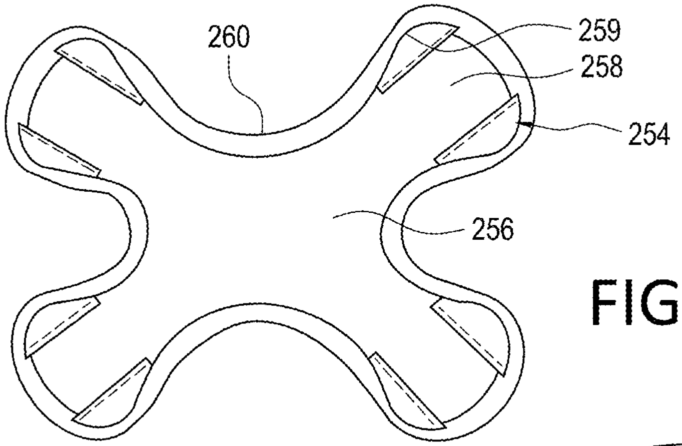
FIG. 10A is a plan view of a sleeve for use in an orthopedic device.
Figure 10B:
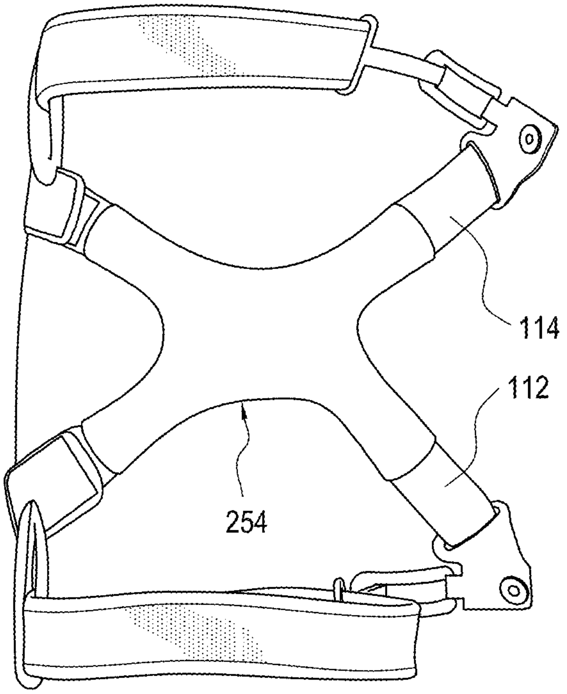
FIG. 10B is a perspective view showing the sleeve of FIG. 10A attached to a strap assembly.
Figure 10C:
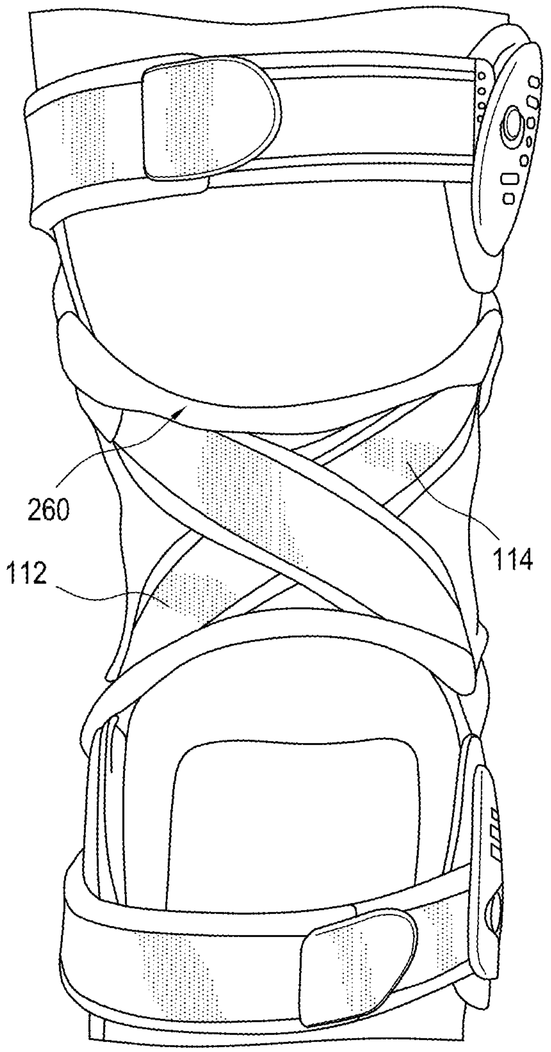
FIG. 10C is a perspective view of the sleeve of FIG. 10A in the orthopedic device of FIG. 1A.

FIGS. 10A-10C depict a sleeve 254 having a main panel 256 and a plurality of end portions 258 having fasteners 259 configured to attach to the first and second dynamic force straps 112, 114. An edge binding 260 surrounds the main panel 256. The sleeve 254 is arranged to extend about the posterior side of the orthopedic device 100, on the inside of the first and second dynamic force straps 112, 114 and adjacent the leg of the user. The sleeve 254 preferably surrounds the popliteal region of the user.

Figure 11A:
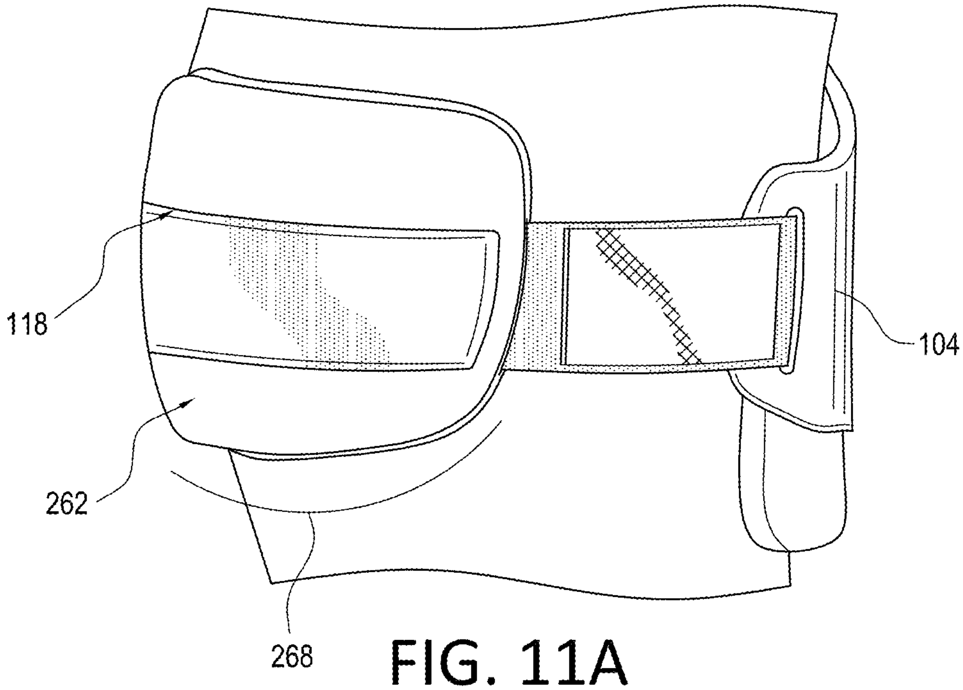
FIG. 11A is a perspective view of a calf pad in the orthopedic device of FIG. 1A.
Figure 11B:
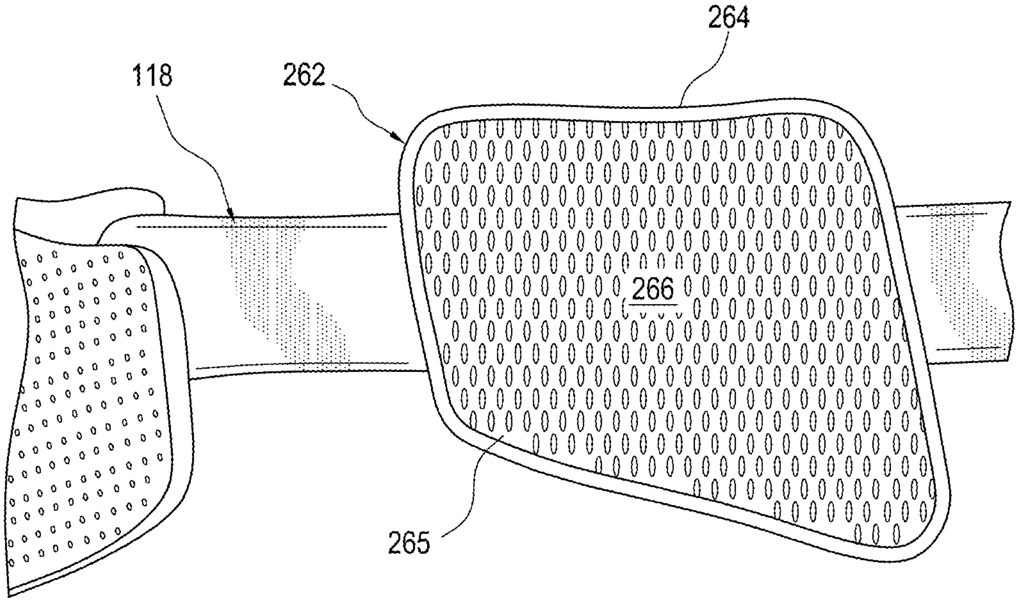
FIG. 11B is a schematic view of the calf pad of FIG. 11A.

FIGS. 11A-11B illustrate a shell 262 located along the second circumferential strap 118. The shell 262 is provided for additional support about the calf and to prevent migration of the orthopedic device 100. The shell 262 is anchored to the second circumferential strap 118, and provides extra surface area to grip and stabilize the orthopedic device 100. By incorporating the shell 262 with the second circumferential strap 118, no additional steps are needed for donning or doffing the orthopedic device 100 with the shell 262.

The shell 262 is preferably formed with a curved profile 268 shaped along a length of the second circumferential strap 118 to better fit the calf of the user. The shell 262 includes a frictional layer 266 located along an inner side thereof for better grip on the user. The shell 262 defines a top portion 264 generally arranged parallel with the second circumferential strap 118 and a bottom portion 265 having a profile extending obliquely and away from the second stability strap 118.

Figure 12A:
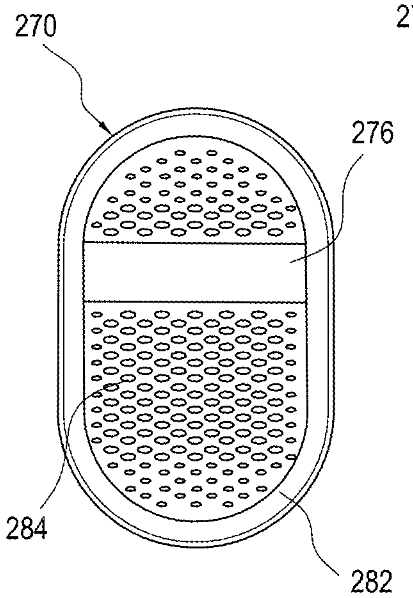
FIGS. 12A-12D are plan views showing variations of hinge covers in the orthopedic device of FIG. 1A.
Figure 12B:
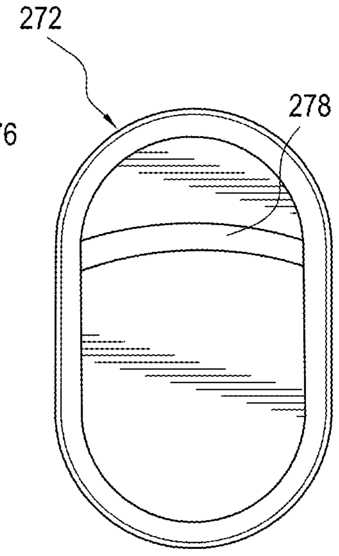
Figure 12C:
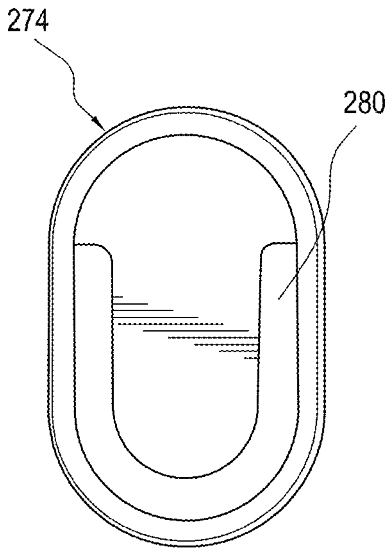

FIGS. 12A-12C show embodiments of hinge covers useable in the hinge 110 of the orthopedic device 100. Preferably, the hinge covers 270, 272, 274 have a textured surface 284 and rounded edges 282. The hinge covers 270, 272, 274 are formed by a soft polymeric material. The hinge covers 270, 272, 274 define a midline marker 276, 278, 280 demarcating alignment for a patella of a user, thereby facilitating easier and more accurate donning of the orthopedic device 100.

Figure 12D:
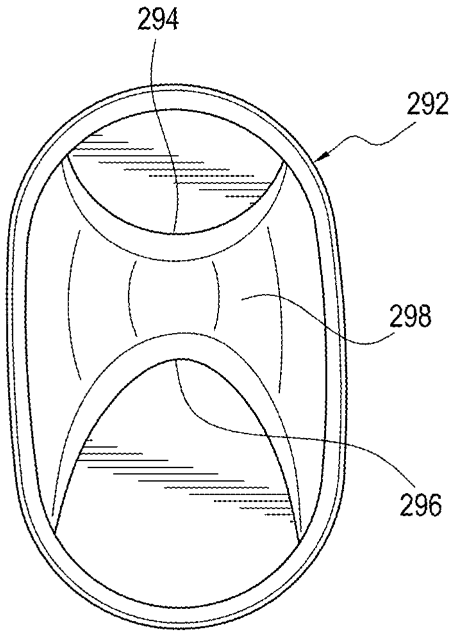

FIG. 12D depicts a hinge cover 292 with tactile elements 294, 296 for covering and protecting the hinge 110. A raised section 298 may be adapted for including a logo or other suitable denotation of the orthopedic device 100 or alignment indicia. The tactile elements 294, 296 may serve as a positioning element (by being adapted for fingers to grip the hinge cover 292) for the hinge 110 to assure that the hinge 110 is properly aligned with the user's knee. The raised section 298 may be used as an alignment element to assure the hinge 110 is properly aligned and can be used to center the hinge 110, with the alignment indicia provided by the raised element 298.

Figure 13A:
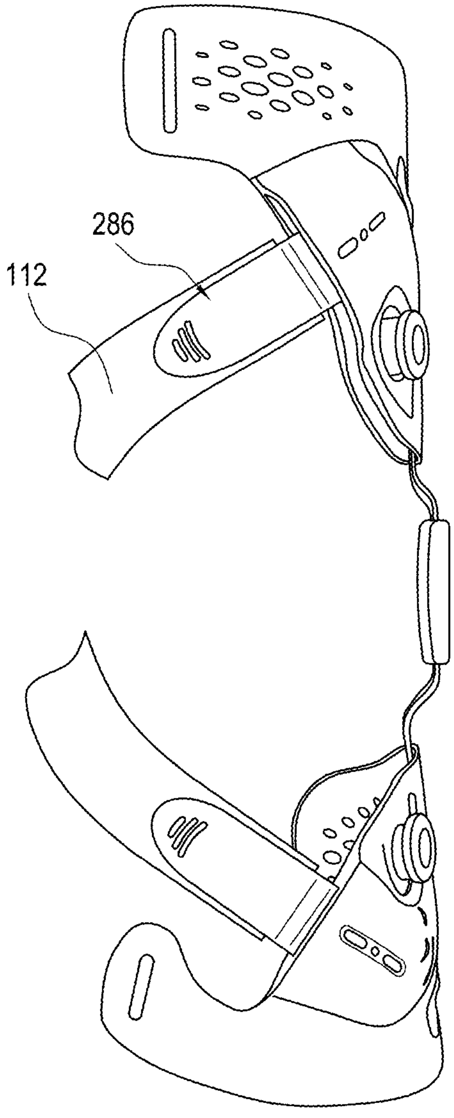
FIG. 13A is a schematic perspective view showing a strap tab connecting the first strap to a first tensioning mechanism.
Figure 13B:
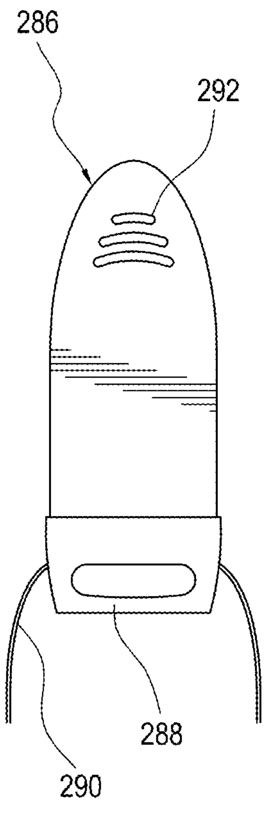
FIG. 13B is a front plan view showing the strap tab in FIG. 13A.
Figure 13C:
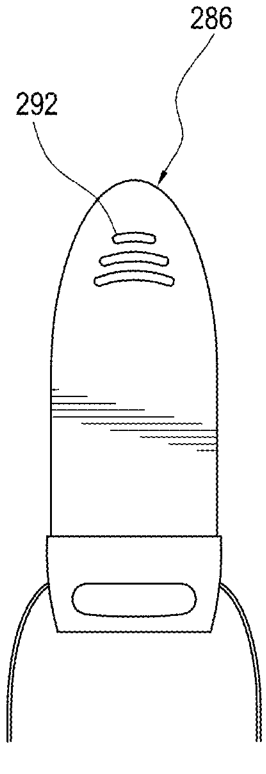
FIG. 13C is a rear plan view showing the strap tab in FIG. 13A.

FIGS. 13A-13C show a tab 286 having a guide 288 extending therefrom for supporting a cable 290 of the tensioning device 120, 122, the cable slidably extending therethrough. The tab 286 is arranged to fasten to the first dynamic force strap 114. The tab 286 is flexible and includes a printed grip 292 on a surface of the tab 286, the printed grip 292 having greater traction properties than material forming the tab 286.

Figure 14A:
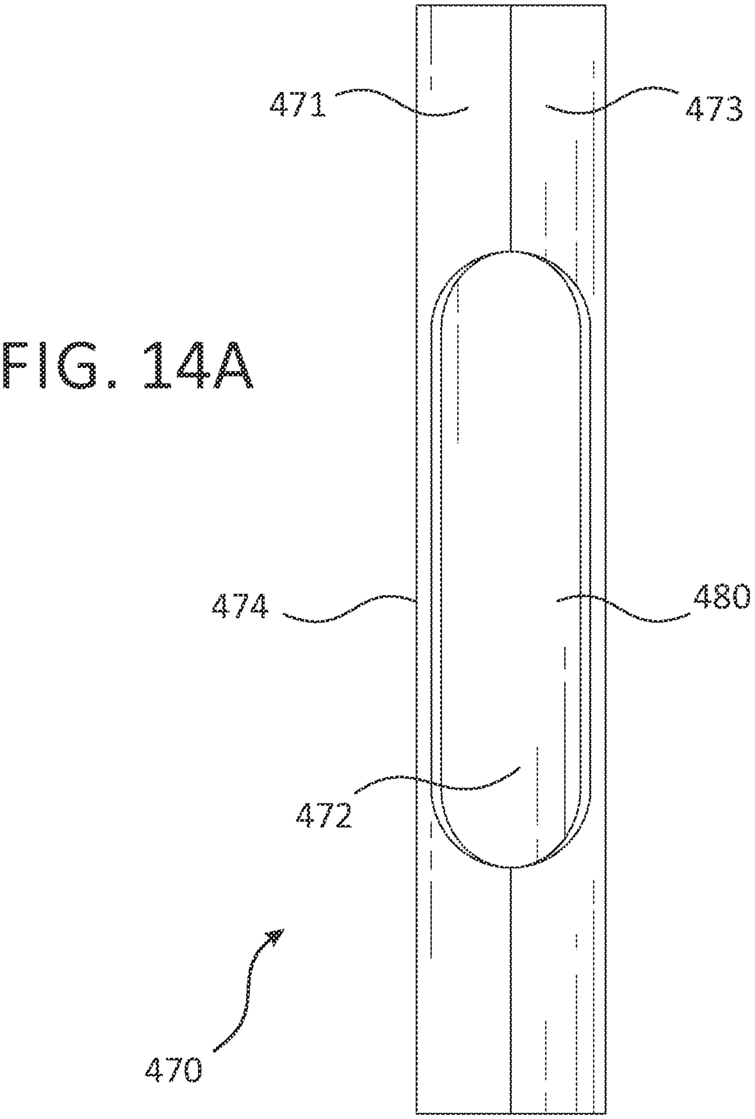
FIG. 14A is a plan view showing a floating pad according to an embodiment of the disclosure.
Figure 14B:
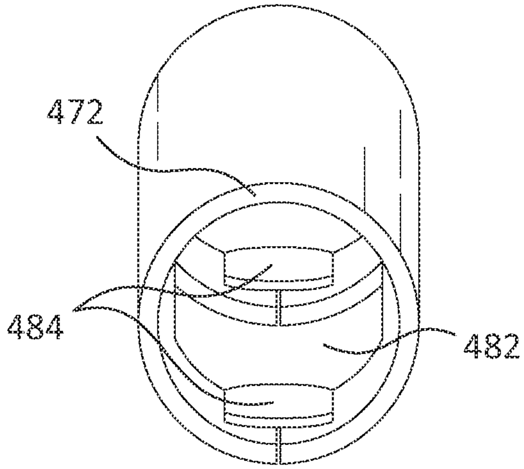
FIG. 14B is a side perspective view of the floating pad of FIG. 14B.
Figure 14C:
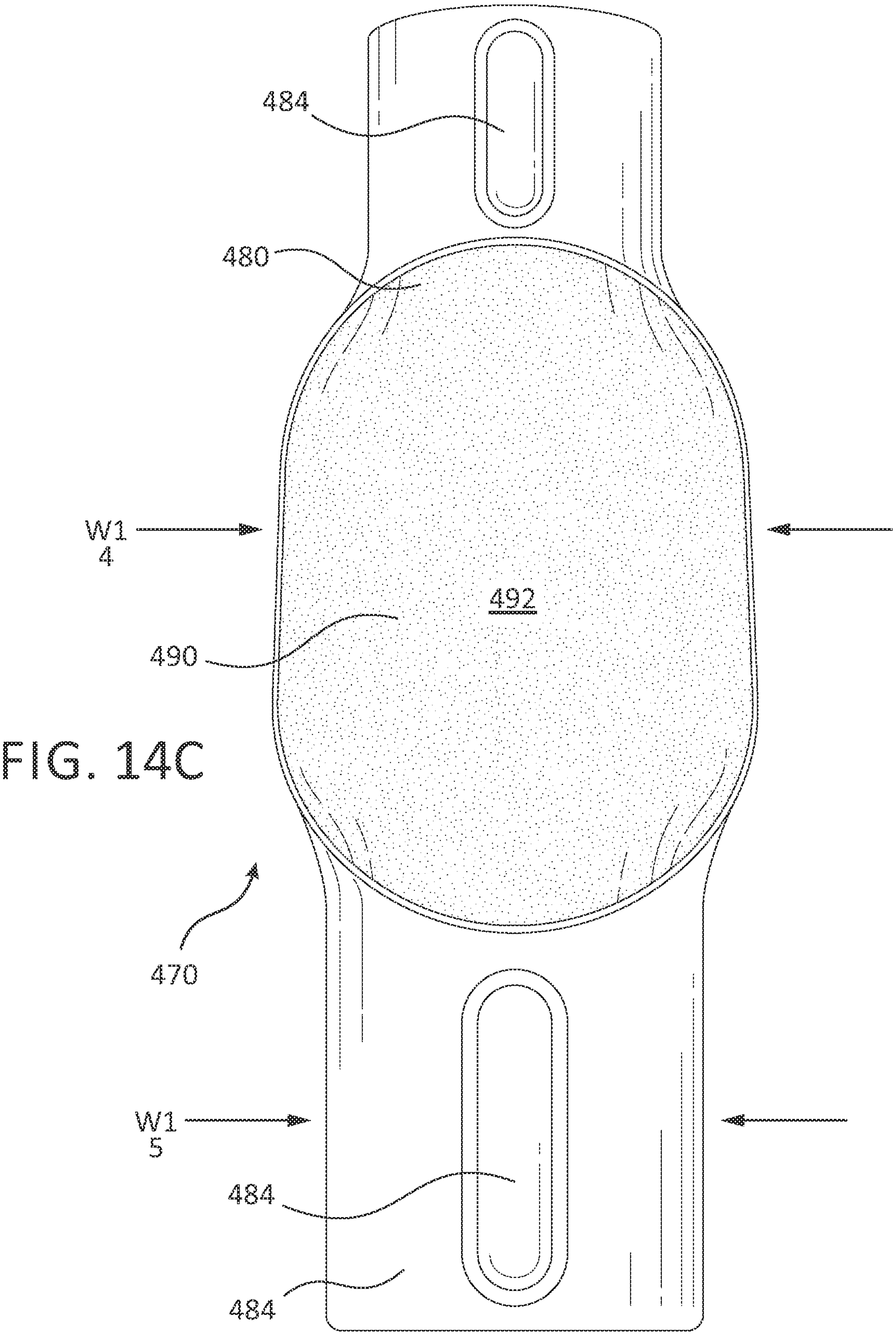
FIG. 14C is a plan view showing a floating pad according to another embodiment of the disclosure.

FIGS. 14A-14C show a floating pad 470 configured for use with an orthopedic device 100 according to embodiments of the disclosure. As shown in the depicted embodiments, a floating pad 470 may be provided to further mitigate and reduce the incidence of pressure points and discomfort along a user's limb resulting from pressure and forces applied by straps, for example the first and second dynamic force straps 112, 114. The floating pad 470 advantageously provides a multi-layer article that may be arranged at a number of convenient locations along one of the dynamic force straps 112, 114 or circumferential straps 116, 118 to evenly distribute pressure. The floating pad 470 allows the straps to perform their intended function (i.e. to apply corrective or unloading forces, especially proximate a joint compartment such as a knee joint) but dissipates the applied force over a larger surface area and/or through a cushioning element so that uncomfortable pressure points are not formed on a user's leg, especially during prolonged periods of use. This advantage becomes increasingly important for older users who may have diminished circulation, or may be otherwise susceptible to discomfort at their skin.

Floating pad 470 comprises multiple layers that facilitate breathability and comfortable functionality. Inner layer 472 which faces away from a user, may comprise a textile material which may be configured with a fastener, such as hook-and-loop-type fastener for grasping a strap material. Middle layer 473 may comprise a soft and/or compressible layer such as foam. In an embodiment, the foam forming middle layer 473 comprises an open cell-type polyetherurethane foam with sufficient thickness to provide cushioning against the forces applied by the straps. An outer layer 474, which contacts the user, may comprise a breathable textile such as doeskin, or a combination of nylon and spandex, or any other material or combination of materials that facilitate a comfortable contact against a user's skin In certain embodiments, floating pad 470 may be arranged in a tubular or circumferential configuration, with outer layer 474 defining the circumferential outwardly facing surface of the floating pad 470, and inner layer 472 defining the circumferential inwardly facing surface of the floating pad 470. The tubular configuration may be formed by joining first and second ends 471, 473 of a flat sheet comprising the outer, middle, and inner layers 474, 473, 472 together, forming a tubular configuration. The floating pad 470, thus arranged in a tubular configuration, advantageously may extend around a strap in a sliding fashion, such that floating pad 470 may be repositioned along numerous discrete locations of a length of a strap at will.

Floating pad 470 may further define a primary aperture 480 extending through each of the outer, middle, and inner layers 474, 473, 472 and configured to allow a user to see the strap extending within a central channel 482 defined between first and second ends of the floating pad 470. The primary aperture 480 may further expose indicia (not shown) printed or otherwise shown on a surface of the strap so that a user may accurately align the floating pad 470 at a desired location. The primary aperture 480 may also assist a user in better grasping surfaces of the strap as the floating pad 470 is adjusted in position.

In certain embodiments, the inner layer 472 may be provided with fasteners or hooks 484 arranged to releasably attach to a surface of a strap so as to hold the floating pad 470 in place. In particular, fasteners or hooks 484 may be located on the inner layer 472 and arranged to attach to a strap. The hooks 484 may comprise nylon or other suitable materials that allow for the floating pad 470 to adequately grab or attach to a material, for example a textile material, of a strap. In other embodiments, the material forming the outer layer 474 may be arranged to releasably attach to a sleeve or other surface.

To further provide a comfortable and pressure-relieving feature against a user's skin, the floating pad 470 may further comprise a pad or cushion element 490 extending outwardly relative to an outer surface of the floating pad 470. The cushion element 490 may define a greater width W14 than a width W15 of the floating pad 470 so as to contact and distribute pressure and forces over a greater portion of a user's skin, thus dissipating the discomfort that can be caused by straps. Cushion element 490 may comprise a textile material 492 enclosing a layer of foam or other soft or compressive material configured to be comfortable against a user's skin. As shown, fasteners 484 may be formed in the layers 472, 473, 474 of the floating pad 470 in order to securely attach the fasteners 484.

The orthopedic device and components provided therewith have improved comfort characteristics due to the absence of features on the interior side of the shells, the overmolded edges of the shells, and the smooth inner surface of the sleeve. In addition, the padding that may be present at the pockets of the sleeve may better distribute pressure exerted on the leg of the user when the straps are tightened.

It is to be understood that not necessarily all objects or advantages may be achieved under any embodiment of the disclosure. Those skilled in the art will recognize that the orthopedic device may be embodied or carried out in a manner that achieves or optimizes one advantage or group of advantages as taught herein without necessarily achieving other objects or advantages as may be taught or suggested herein.

The skilled artisan will recognize the interchangeability of various disclosed features. In addition to the variations described herein, other known equivalents for each feature can be mixed and matched by one of ordinary skill in this art to construct an orthopedic device in accordance with principles of the present disclosure. It will be understood by the skilled artisan that the features described herein may be adapted to other types of orthopedic devices. Hence this disclosure and the embodiments and variations thereof are not limited to knee braces, but can be utilized in any orthopedic devices.

Although this disclosure describes certain exemplary embodiments and examples of an orthopedic device, it nevertheless will be understood by those skilled in the art that the present disclosure extends beyond the specifically disclosed knee brace embodiments to other alternative embodiments and/or uses of the disclosure and obvious modifications and equivalents thereof. It is intended that the scope of the present disclosure should not be limited by the particular disclosed embodiments described above, and may be extended to orthopedic devices and supports, and other applications that may employ the features described herein.

The invention claimed is:

1. An orthopedic device, comprising:

a frame assembly including a shell;

a first strap having a first end slidably connecting to a first location on the frame assembly at the shell and a second end connecting to a second location on the frame assembly;

wherein the shell has a shell body formed of a rigid or semi-rigid material;

wherein the shell body defines a varying thickness along a length of the shell including at least one zone having a thinner thickness than in areas outside of the at least one zone;

wherein the shell body defines a varying thickness according to a height of the shell body, such that a thickness at a first portion of a height of the shell body along the length of the shell body is different than a second portion of the height at a same location along the length; and wherein the shell is configured to be arranged to contour about a cavity draw direction or about a user's leg, in at least first, second and third primary planes along the length of the shell;

wherein the shell further defines a peripheral edge formed of a more flexible material extending about the shell body, such that the peripheral edge is more flexible than the shell body;

wherein the peripheral edge extends over and along both an inner surface and an outer surface of the shell body, wherein an extension of the peripheral edge over and along the inner surface is more than the extension of the peripheral edge over and along an outer surface.

2. The orthopedic device of claim 1, wherein the shell forms a perforated region having a plurality of openings arranged in at least one pattern according to at least two predetermined directions.

3. The orthopedic device of claim 2, wherein a first pattern of the at least one pattern is proximate a strap slot formed by a periphery of the shell body, wherein the shell is configured to be arranged to contour to anatomy of a user by yielding to anatomical contours while the shell maintains its integrity.

4. The orthopedic device of claim 2, wherein the at least one pattern defines a plurality of openings having a greater size in a middle of the at least one pattern and taper in size toward an end portion of the at least one pattern.

5. The orthopedic device of claim 2, wherein the at least one pattern is arranged in a diagonal arrangement configured to anatomically follow contours by which the shell body is fitted to bend on a user, wherein the at least one pattern includes localized patterns defined by multiple rows of the openings, defined in part by a sequential difference in sizes of the openings.

6. The orthopedic device of claim 2, wherein the at least one pattern includes a first dimension defined by a first length of the openings having a greater length than a second dimension defined by a first width, the first dimension leading in a first direction to increase flexure, and the second dimension arranged in a second direction whereat flexure is inhibited.

7. The orthopedic device of claim 1, wherein the second primary plane defines a slot for receiving a strut, which forms part of the frame assembly.

8. The orthopedic device of claim 7, wherein the second primary plane defines a hook for receiving a buckle assembly adapted to secure onto the shell at the second primary plane.

9. The orthopedic device of claim 8, wherein the hook is arranged generally in at least one of two predetermined directions.

10. The orthopedic device of claim 1, further comprising a first tensioning mechanism including a dial tensioner mounted onto the first shell and movable relative to the first shell to incrementally adjust a length of a cable windable about the dial tensioner and secured to first strap between the locations on the frame assembly;

wherein the second primary plane defines a base for receiving the tensioning mechanism movable relative to the shell.

11. The orthopedic device of claim 10, wherein the second primary plane defines at least one channel in the shell through which the cable extends and at least partially enclosed by a closure.

12. The orthopedic device of claim 11, wherein the thickness is variable along the length according to features defined by the shell including a strut slot, the base and the at least one cable guide.

13. The orthopedic device of claim 1, wherein a thickness of the first primary plane is less than a thickness of the second primary plane;

wherein the thickness varies along the height of the shell;

wherein the third primary plane includes a strap extension defined elongate along the length of the shell;

wherein the third primary plane is longer than the first primary plane.

14. The orthopedic device of claim 13, wherein the strap extension defines a strap slot adapted to receive a circumferential strap arranged to connect to opposite sides of the frame assembly.

15. The orthopedic device of claim 1, wherein the peripheral edge has a first width at a first location, and a second width at a second location, the first width being greater than the second width.

16. The orthopedic device of claim 1, wherein the peripheral edge has an increased profile configured to be arranged to extend about a user's tibia to provide additional flexure and padding of the shell about the user's tibia.

17. The orthopedic device, of claim 1, wherein the first primary plane is arranged posteriorly of an anterior-posterior plane, and defines a perforation region including at least one opening.

18. The orthopedic device of claim 1, wherein the second primary plane is arranged along an anterior-posterior plane of the orthopedic device.

19. The orthopedic device of claim 1, further comprising a frame extension extending along a periphery of the shell, the frame extension extending adjacently along an entirety of the periphery of the shell;

wherein the frame extension defines an upper extension adjacent a periphery of the shell, a portion of the upper extension extending underneath a segment of a circumferential strap arranged to connect to opposite sides of the frame assembly.

* * * * *